United States Patent
Lindars et al.

(10) Patent No.: US 10,413,685 B2
(45) Date of Patent: Sep. 17, 2019

(54) VAPORIZER

(71) Applicant: Iconic Ventures, Inc., Lake Oswego, OR (US)

(72) Inventors: Michael Lindars, Portland, OR (US); Robert Niemeyer, Tigard, OR (US)

(73) Assignee: Iconic Ventures, Inc., Portland, OR (US)

( * ) Notice: Subject to any disclaimer, the term of this patent is extended or adjusted under 35 U.S.C. 154(b) by 0 days.

(21) Appl. No.: 15/950,083

(22) Filed: Apr. 10, 2018

(65) Prior Publication Data

US 2018/0289909 A1 Oct. 11, 2018

Related U.S. Application Data

(60) Provisional application No. 62/483,868, filed on Apr. 10, 2017, provisional application No. 62/626,451, filed on Feb. 5, 2018.

(51) Int. Cl.
*A61M 15/06* (2006.01)
*A61M 15/00* (2006.01)
(Continued)

(52) U.S. Cl.
CPC ............. *A61M 15/06* (2013.01); *A61K 9/007* (2013.01); *A61K 9/0078* (2013.01); *A61K 47/44* (2013.01);
(Continued)

(58) Field of Classification Search
CPC .... A61M 15/06; A61M 11/04; A61M 11/041; A61M 11/042; A61M 15/0021;
(Continued)

(56) References Cited

U.S. PATENT DOCUMENTS

| 4,913,169 A | 4/1990 | Templeton |
| 4,989,619 A | 2/1991 | Clearman et al. |

(Continued)

FOREIGN PATENT DOCUMENTS

| CA | 2931486 A1 | 5/2015 |
| WO | 2006015148 A1 | 2/2006 |

(Continued)

OTHER PUBLICATIONS

Vape Pen Mesh Coil, accessed Oct. 2, 2018, pp. 1-12, www.smoktech.com.

(Continued)

*Primary Examiner* — Jan Christopher L Merene
*Assistant Examiner* — Elliot S Ruddie
(74) *Attorney, Agent, or Firm* — Mackey Law Firm PLLC

(57) ABSTRACT

A vaporizer can include a reservoir for holding oil, a chamber for holding vapor, a feeder for feeding oil from the reservoir to the chamber, and a heater for heating oil. A feeder can be configured to feed oil from the reservoir to the chamber by capillary action. A vaporizer can include a plug sealingly coupled to the reservoir and configured to slide relative to at least a portion of the reservoir. A heater can include at least one of a laser, a resistance heater, a wire, a coil, a wire at least partially disposed in a housing, and a combination thereof. A vaporizer can include a controller and can be configured to heat a heater to a first temperature for a first time period, reduce the temperature of the heater, and maintain the heater at a second temperature for a second time period.

20 Claims, 19 Drawing Sheets

(51) Int. Cl.
*A61M 11/04* (2006.01)
*A61K 9/00* (2006.01)
*A61K 47/44* (2017.01)
*A24F 47/00* (2006.01)

(52) U.S. Cl.
CPC ...... *A61M 11/042* (2014.02); *A61M 15/0021* (2014.02); *A24F 47/008* (2013.01); *A61M 2205/3368* (2013.01); *A61M 2205/368* (2013.01); *A61M 2205/3653* (2013.01)

(58) Field of Classification Search
CPC .. A61M 2205/3368; A61M 2205/3372; A61M 2205/3653; A61M 2205/368; A61M 11/007; A61K 9/007; A61K 9/0073; A61K 9/0078; A61K 47/44; A24F 47/00; A24F 47/002; A24F 47/004; A24F 47/008
USPC ............ 128/202.21; 131/273, 194, 299, 300, 131/309, 310, 329, 900, 901, 902, 903
See application file for complete search history.

(56) References Cited

U.S. PATENT DOCUMENTS

| | | | |
|---|---|---|---|
| 5,137,034 | A | 8/1992 | Perfetti et al. |
| D682,465 | S | 5/2013 | Yeom |
| D747,548 | S | 1/2016 | Mayor |
| 9,320,300 | B2 | 4/2016 | Hon |
| D760,952 | S | 7/2016 | Mayor |
| D787,114 | S | 5/2017 | Scott |
| D805,687 | S | 12/2017 | Perez et al. |
| 9,943,108 | B2 | 4/2018 | Lord |
| 9,986,760 | B2 | 6/2018 | Macko et al. |
| 10,004,682 | B2 | 6/2018 | Muzzio et al. |
| 10,034,990 | B2 | 7/2018 | Mccullough |
| D827,196 | S | 8/2018 | Sudlow |
| D827,920 | S | 9/2018 | Fornarelli |
| 2012/0093902 | A1 | 4/2012 | Artiga-Gonzalez et al. |
| 2013/0192623 | A1 | 8/2013 | Tucker et al. |
| 2013/0255702 | A1 | 10/2013 | Griffith, Jr. et al. |
| 2014/0069424 | A1* | 3/2014 | Poston ................. A24F 47/008 128/202.21 |
| 2014/0299137 | A1* | 10/2014 | Kieckbusch .......... A24F 47/008 131/328 |
| 2015/0136124 | A1 | 5/2015 | Aronie et al. |
| 2015/0208728 | A1 | 7/2015 | Lord |
| 2015/0272216 | A1* | 10/2015 | Dai ....................... A61M 15/06 131/328 |
| 2016/0295914 | A1 | 10/2016 | Jordil et al. |
| 2016/0360790 | A1 | 12/2016 | Calfee et al. |
| 2017/0156399 | A1 | 6/2017 | Freeman et al. |
| 2017/0215481 | A1 | 8/2017 | Li et al. |
| 2017/0224018 | A1 | 8/2017 | Li et al. |
| 2017/0231286 | A1 | 8/2017 | Borkovec et al. |
| 2017/0340018 | A1 | 11/2017 | Thorens |
| 2017/0360095 | A1 | 12/2017 | Batista |
| 2018/0014576 | A1 | 1/2018 | White |
| 2018/0020723 | A1 | 1/2018 | Davis et al. |
| 2018/0132534 | A1 | 5/2018 | Reevell |
| 2018/0162769 | A1 | 6/2018 | Peuchert et al. |
| 2018/0177231 | A1 | 6/2018 | Woodbine et al. |
| 2018/0177240 | A1 | 6/2018 | Duque et al. |
| 2018/0206553 | A1 | 7/2018 | Reevell |
| 2018/0220710 | A1 | 8/2018 | Marks et al. |
| 2018/0221605 | A1 | 8/2018 | Marks et al. |
| 2018/0255834 | A1 | 9/2018 | Dillmann et al. |
| 2018/0255835 | A1 | 9/2018 | Crowe et al. |
| 2018/0289909 | A1 | 10/2018 | Lindars et al. |
| 2018/0295886 | A1 | 10/2018 | Freeman et al. |
| 2018/0333547 | A1 | 11/2018 | Freeman et al. |
| 2019/0029318 | A1 | 1/2019 | Schneider |

FOREIGN PATENT DOCUMENTS

| | | |
|---|---|---|
| WO | 2011146174 A2 | 2/2012 |
| WO | 2015107552 A1 | 7/2015 |
| WO | 2017001352 A3 | 2/2017 |
| WO | 2018037245 A1 | 3/2018 |

OTHER PUBLICATIONS

Lucky Edibles—Cannabis Infused Flavored Mints, accessed Nov. 20, 2018, www.luckyedibles.com.
Statement of Trademark Registration of a Reporting Entity, Jul. 28, 2014, ID No. 20141459355, Colorado Secretary of State, USA.
Statement of Trademark Registration of a Reporting Entity, Sep. 15, 2016, ID No. 20161623092, Colorado Secretary of State, USA.
Statement of Trademark Registration of a Reporting Entity, Oct. 31, 2016, ID No. 20161743535, Colorado Secretary of State, USA.
Statement of Trademark Registration of a Reporting Entity, Oct. 31, 2016, ID No. 20161743695, Colorado Secretary of State, USA.
International Search Report and Written Opinion dated May 16, 2019 for International Application No. PCT/US2019/016706.
International Search Report and Written Opinion dated Jan. 17, 2019 for International Application No. PCT/US2018/026976.
International Search Report and Written dated Jul. 11, 2019 for International Application No. PCT/US2019/026857.

* cited by examiner

VAPORIZER

CROSS REFERENCE TO RELATED APPLICATIONS

This application claims the benefit of U.S. Provisional Patent Application No. 62/483,868 filed Apr. 10, 2017 and U.S. Provisional Patent Application No. 62/626,451 filed Feb. 5, 2018, the entire contents of which are hereby incorporated by reference into this disclosure.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The present disclosure relates generally to vaporizers and more specifically relates to vaporizers for converting oil to a mist for inhalation by a user.

Description of the Related Art

A vaporizer can be used to convert oil or another substance, such as a substance that contains medication or other compounds, to a vapor or mist for inhalation by a user. Oils can be used to prevent damage to medications that may be sensitive to solvents or propellants used in applications like asthma inhalers, or for medications or compounds that cannot be dissolved in water. However, at least some conventional vaporizers may suffer from one or more shortcomings, such as burning or carbonization of the oil, excessive wicking, leaking, or clogging. For example, burning or carbonization of oil may occur when a supply of oil is locally depleted relative to a heating coil, which can allow the coil in the area of depletion to overheat, which can include becoming red hot. When oil flows into such a depleted area and comes in contact with the over-heated coil, burning of the oil can occur, which can generate smoke that may reach air flow through the device. In at least some cases, such burning may result in undesirable tastes or flavors during use of the device, which can continue for some time or even for the life of the device, and which can effectively render the device no longer useable. Carbonization can result in carbon buildup, e.g., on the wick or heating coil of the device, which can foul or prevent proper operation or continued use of a vaporization device. Carbonization can also be indicative that the oil has been overheated, such as by having been heated to a point that some damage or change to the chemical nature of the oil has occurred. Carbonization may also result in undesirable compounds being present in the vapor or air flow exiting a vaporizer during use, which may include carcinogenic or otherwise dangerous compounds.

As another example, at least some conventional vaporizers include wicking devices for transferring oil from the storage reservoir to an area for contact with the heating element. However, such wicking devices can result in leaking of oil from the vaporizer, such as onto a user's hand or clothing. Excessive wicking can fowl a heating element, such as by providing too much fluid to heat to the vaporization point. Excessive wicking may also clog air channels within the device or leave oil exposed to air, which may result in malfunctions or, e.g., allow volatile medication dissolved in the oil to evaporate. In some cases, such evaporation may cause the oil's viscosity to change to a point that prevents the oil from being re-liquefied or vaporized within the device. Excessive wicking and clogging may lead to the loss of some or all of the oil contained in the vaporizer, or even render the vaporizer inoperable such that repair or replacement may be needed. As further examples, in some cases, the oil used in the vaporizer can be corrosive (e.g., having a PH between 8 and 11.5) and may come into contact with metal parts within the device, which can result in a metallic taste that may be undesirable to some users. Additionally, conventional devices may lack a manner of recycling or trapping condensed oil within the device for prevent waste or leaking of the oil.

Accordingly, a need exists in the art for an improved vaporizer. The disclosures and teachings herein are directed to systems and methods for improved vaporizers, portions thereof, devices for use therewith and corresponding methods.

BRIEF SUMMARY OF THE INVENTION

A vaporizer according to the present disclosure can include one or more portions or components for at least partially vaporizing a substance, such as oil, water or another material capable of being vaporized (whether liquid, solid, or otherwise), to form a mist capable of being inhaled by a user of the vaporizer. As will be understood by a person of ordinary skill in the art having the benefits of the present disclosure, commercially available substances for vaporization commonly include oils or other materials in liquid form; however, that need not be the case, and such materials can alternatively (or collectively) exist in a non-liquid form, such as, for example, a solid or semi-solid form. For purposes of convenience, the term "oil" is used in this disclosure to refer collectively to any substance capable of vaporization by way of an apparatus or method according to the disclosure, whether in liquid, solid, or another form, and whether now known or later developed.

In at least one embodiment, a vaporizer can include a plurality of portions that cooperate with one another, such as, for example, a feed mechanism, a vaporization chamber, a heat source, and a power supply. One or more of such portions can, but need not, be disposable or replaceable, separately or in combination, in whole or in part. In at least one embodiment, a feed mechanism and vaporization chamber can be at least partially incorporated into a disposable portion of a vaporizer that can be interchanged with one or more other portions of the device, such as a body or frame for coupling one or more vaporizer components to one another. In at least one embodiment, one or more portions of a vaporizer can be refillable, such as, for example, a feed mechanism or a portion of a feed mechanism for housing or storing oil or another substance to be vaporized, which can include housing a component that houses or otherwise stores such substance.

In at least one embodiment, a feed mechanism can be adapted for receiving, storing and feeding one or more oils into a vaporization chamber, separately or in combination, in whole or in part. In at least one embodiment, a feed mechanism can be adapted for routing fluid from one location to another, which can include comprising one or more conduits or flow paths, such as air flow channels for routing vapor from a vaporization chamber to a mouthpiece or other portion of a vaporizer and a mouth piece for routing vapor from within a vaporizer to a user.

In at least one embodiment, a vaporization chamber can be adapted for supporting generation of oil vapor and for mixing vapor with air flowing through a vaporizer. A vaporization chamber can be adapted for collecting condensed vapor, trapping oil overflow, such as from excessive wicking, and preventing excessive wicking or leaked oils from getting to the outside of the vaporizer, separately or in combination, in whole or in part.

In at least one embodiment, a heat source can be adapted for heating oil sufficiently to vaporize at least a portion of the oil, which can be any portion of the oil according to a particular application. In at least one embodiment, a heat source can be or include an electrically powered source of heated air, which can be directed at a feed mechanism for generating vaporized oil. In at least one embodiment, a heat source can be or include a heating coil, such as a coil made from a nickel chrome alloy or another suitable material, which can be heated via battery or another electrical power source. In at least one embodiment, a heat source can be or include one or more other sources, such as a laser or a light emitting diode (LED) having a light frequency sufficient for heating an oil in accordance with a particular application or embodiment of a vaporizer according to the disclosure.

In at least one embodiment, a vaporizer can include a power supply for generating heat for vaporization of the oil, such as, for example, a battery or other self-contained electric power source. A vaporizer can include one or more switches, such as a switch for turning on and off power to one or more portions of the device, an internal or other time-out switch for turning off the power if power is applied to one or more portions of the device for longer than a set time period (e.g., ten seconds, or a longer or shorter time period, which can be any time period according to an application). In at least one embodiment, a vaporizer can include an air flow switch, such as a pressure sensor, for allowing power to be applied, e.g., to a heat source when air is flowing through the vaporizer and/or preventing application of power when air is not flowing through one or more portions of the vaporizer. In at least one embodiment, a power supply can be or include a battery, such as a Lithium cell or other battery. In at least one embodiment, a vaporizer can include one or more controllers for controlling one or more aspects of vaporizer operation, such as, for example, for controlling power applied to a heating element, operation time, voltage or current applied to a heating element, recharging of a battery cells, or another aspect of operation, separately or in combination, in whole or in part.

A vaporizer can include a reservoir for holding oil, a chamber for holding vapor, a feeder for feeding oil from the reservoir to the chamber, and a heater for heating oil. A feeder can be configured to feed oil from the reservoir to the chamber by capillary action. A feeder can include a wick that can be at least one of ceramic, sintered metal, aluminum oxide, which can include aluminum oxide held together with quartz glass or another bonding material or agent, and a combination thereof. A vaporizer can include a plug sealingly coupled to the reservoir and configured to slide relative to at least a portion of the reservoir. A plug can be configured to move from a first end of the reservoir toward the feeder as a volume of oil within the reservoir decreases. A plug can be configured to at least partially resist sinking into a volume of oil within the reservoir, such as by at least partially floating or by way of being mechanically or otherwise constrained. A vaporizer can include a feed control mount coupled to the reservoir and the chamber and configured to hold the feeder in fluid communication with the reservoir and the chamber. A heater can include at least one of a laser, a resistance heater, a wire, a coil, a wire at least partially disposed in a housing, and a combination thereof.

A vaporizer can include a controller coupled to the heater and can be configured to heat the heater to a first temperature for a first time period, reduce the temperature of the heater, and maintain the heater at a second temperature for a second time period. A first time period can be shorter or longer than a second time period. A controller can be configured to control one or more heaters by at least one of controlling voltage supplied to the heater, controlling current supplied to the heater, and a combination thereof. A controller can be configured to control one or more heaters by pulse width modulation of power supplied to the heater(s).

A reservoir can be disposed in a reservoir housing, and a reservoir housing can include a first flow passage or other passages in fluid communication with a chamber or other portion of a vaporizer. A vaporizer can include a mouthpiece coupled to the reservoir housing, and a mouthpiece can include a second flow passage or other passages in fluid communication with a first flow passage. A heater can be configured to heat at least a portion of the feeder. A vaporizer or portion thereof, such as a feeder, can be, include, or be configured to couple with a porous tab adapted to store oil in one or more pores thereof. A tab can be at least one of ceramic, sintered metal, aluminum oxide and a combination thereof. A vaporizer can include a filter coupled to the feeder or another component, such as a feed control mount, and a heater can be configured to heat at least a portion of the filter.

A vaporizer can include a reservoir housing comprising a reservoir configured to hold oil and a first flow passage fluidically separate from the reservoir, a feed control mount coupled to the reservoir housing, a chamber coupled to the feed control mount and configured to hold vapor, an air inlet disposed in the chamber, a feeder coupled to the feed control mount and disposed in fluid communication with both the reservoir and the chamber, a heater configured to heat oil disposed within the chamber, and a plug slideably and sealingly coupled to the reservoir.

A feeder can be configured to feed oil from the reservoir to the chamber, which can include by capillary action. A plug can be configured to move from a first end of the reservoir toward the feeder as a volume of oil within the reservoir decreases, such as during use of the vaporizer. A vaporizer can include a controller coupled to the heater and can be configured to heat the heater to a first temperature for a first time period, reduce the temperature of the heater, and maintain the heater at a second temperature for a second time period. A second time period can be shorter than, longer than, or equal to a first time period.

DETAILED DESCRIPTION

Figure 1:
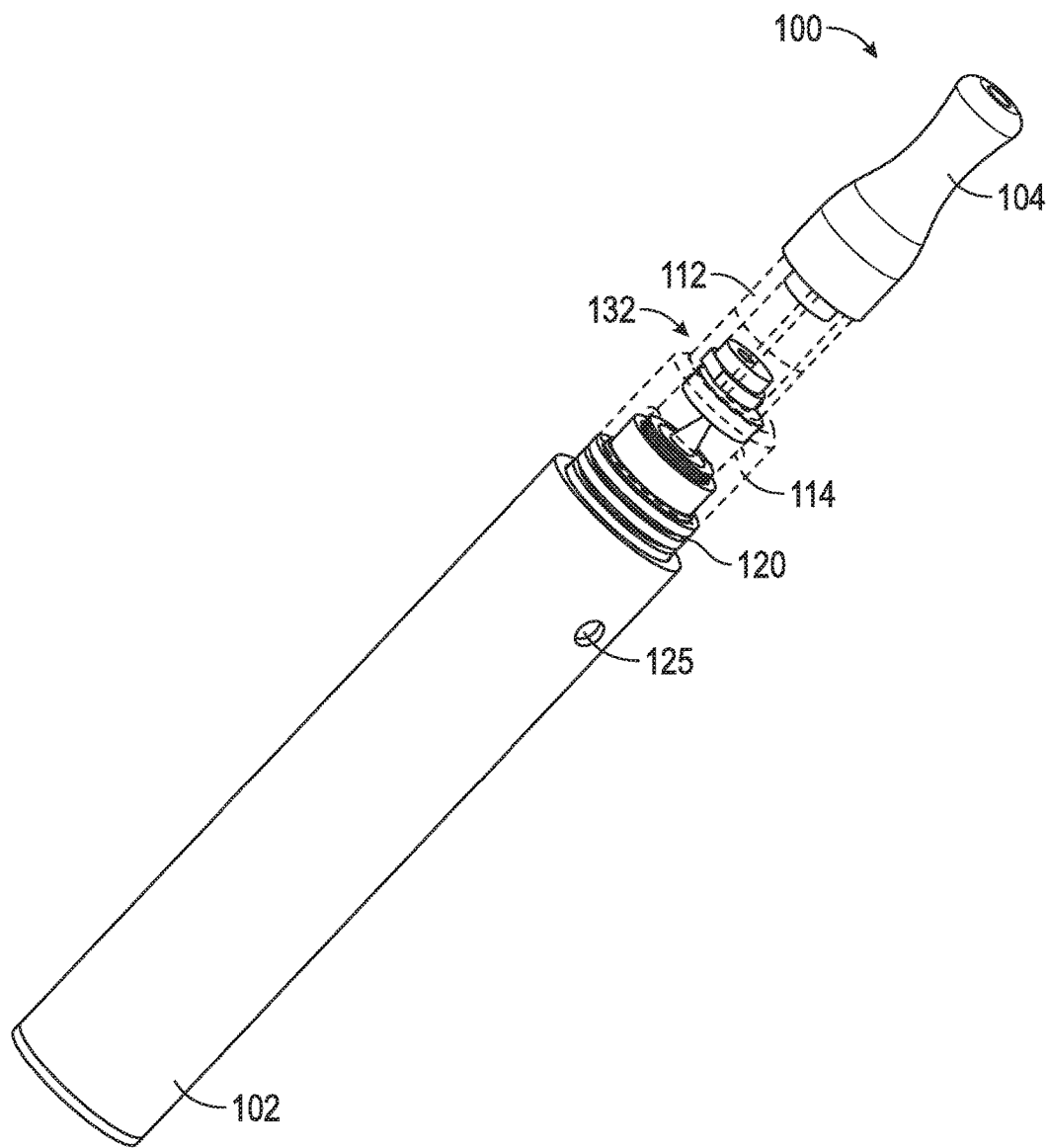
FIG. 1 is a perspective view of one of many embodiments of a vaporizer according to the disclosure.

The Figures described above and the written description of specific structures and functions below are not presented to limit the scope of what Applicants have invented or the scope of the appended claims. Rather, the Figures and written description are provided to teach any person skilled in the art to make and use the invention(s) for which patent protection is sought. Those skilled in the art will appreciate that not all features of a commercial embodiment of the disclosure are described or shown for the sake of clarity and understanding. Persons of skill in this art will appreciate that the development of an actual commercial embodiment incorporating aspects of the present disclosure can require numerous implementation-specific decisions to achieve the developer's ultimate goal for the commercial embodiment(s). Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in the art having the benefits of this disclosure.

The embodiment(s) disclosed and taught herein are susceptible to numerous and various modifications and alternative forms. The use of a singular term, such as, but not limited to, "a," is not intended as limiting of the number of items. The use of relational terms, such as, but not limited to, "top," "bottom," "front," "rear," "left," "right," "upper," "lower," "down," "up," "side," "first," "second," "inlet," "outlet" and the like are used in the written description for clarity in specific reference to the Figures and are not intended to limit the scope of the disclosure or the appended claims unless otherwise indicated. The terms "couple," "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and can further include without limitation integrally forming one member with another in a unity fashion. The coupling can occur in any direction, including rotationally. The terms "include" and "such as" are illustrative and not limitative, and the word "can" means "can, but need not" unless otherwise indicated. The term "end" can, but need not, be or include a terminal end unless otherwise indicated. Notwithstanding any other language in the present disclosure, the embodiment(s) shown in the drawings are examples presented for purposes of illustration and explanation and are not the only embodiments of the subject(s) hereof.

Applicants have created systems and methods for vaporizing oil, such as cannabidiol (CBD) oil and derivatives thereof, tetrahydrocannabinol (THC) oil, or other oils having medication therein, for human inhalation. In at least one embodiment, a system for vaporizing oil, or a vaporizer, can include a reservoir for holding oil, a feeder for feeding oil, a chamber for supporting vaporization of oil, an air inlet, an air outlet, a flow path between the inlet and the outlet, a heater for heating oil, and a power source for powering the heater. Additional functions and aspects of the systems and methods of the present disclosure are described in further detail below with reference to the Figures.

Figure 2:
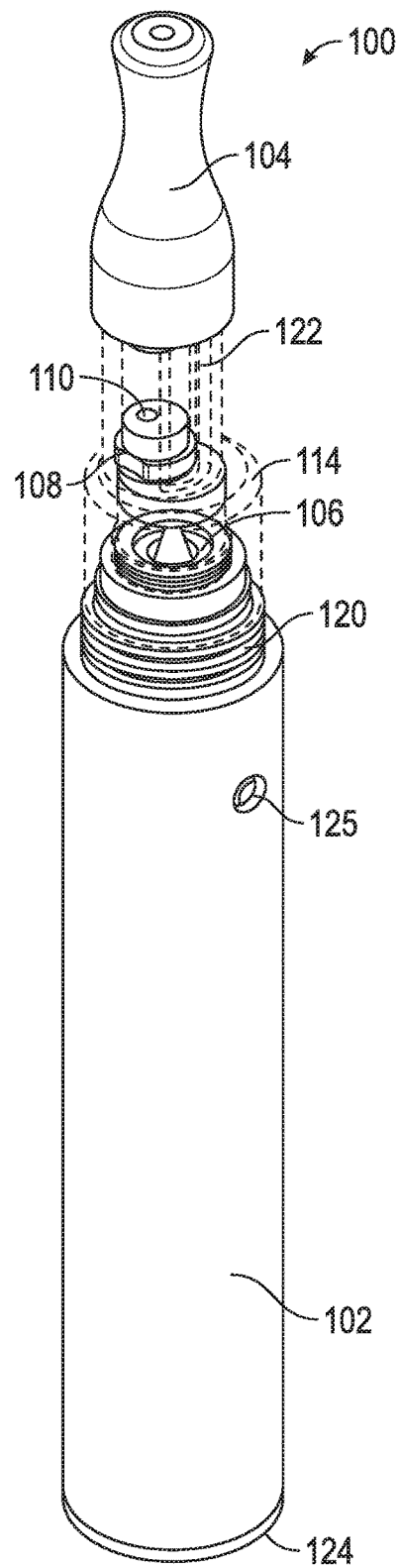
FIG. 2 is an isometric view of the vaporizer of FIG. 1.
Figure 3:
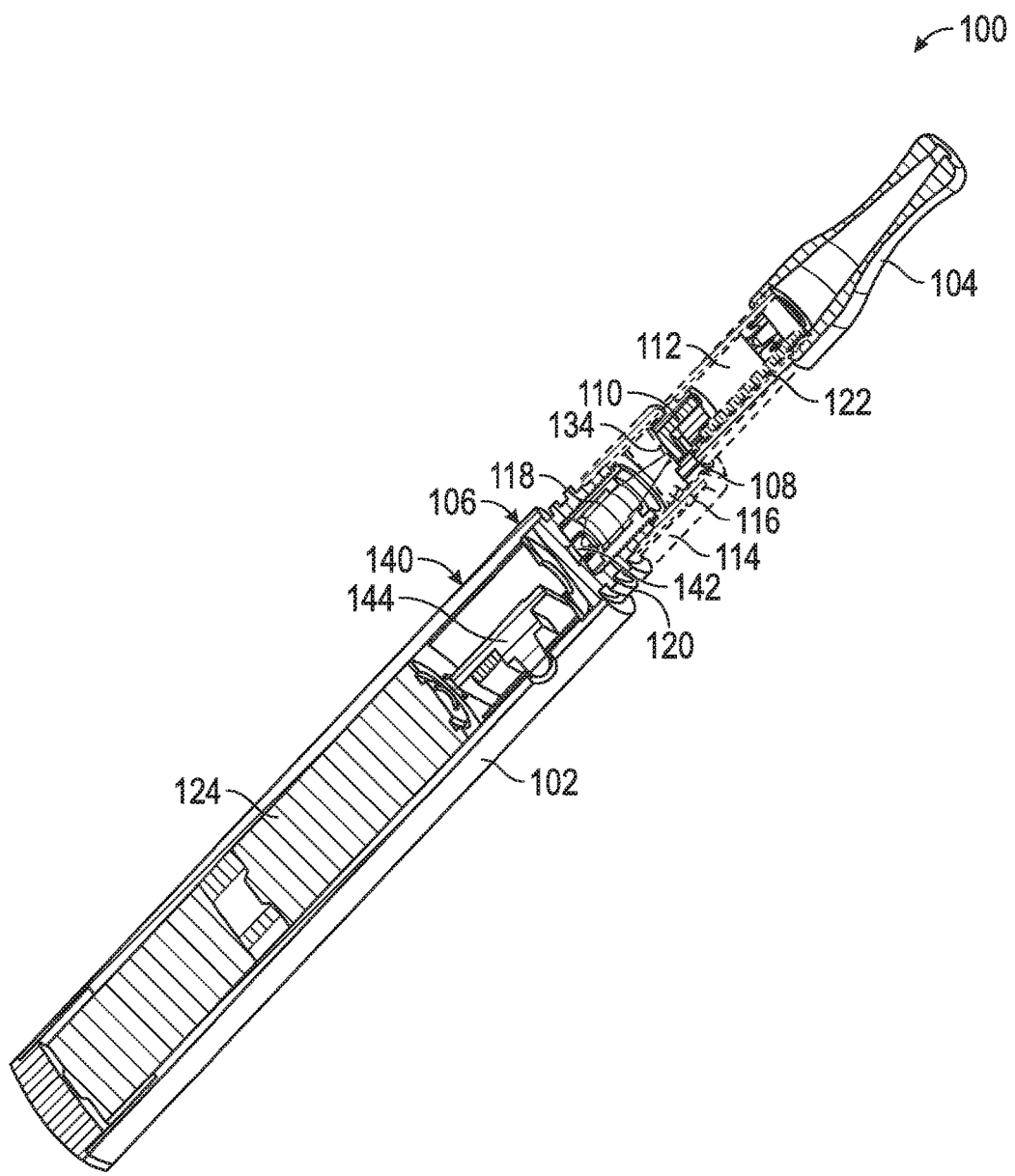
FIG. 3 is a cross-sectional perspective view of the vaporizer of FIG. 1.
Figure 4:
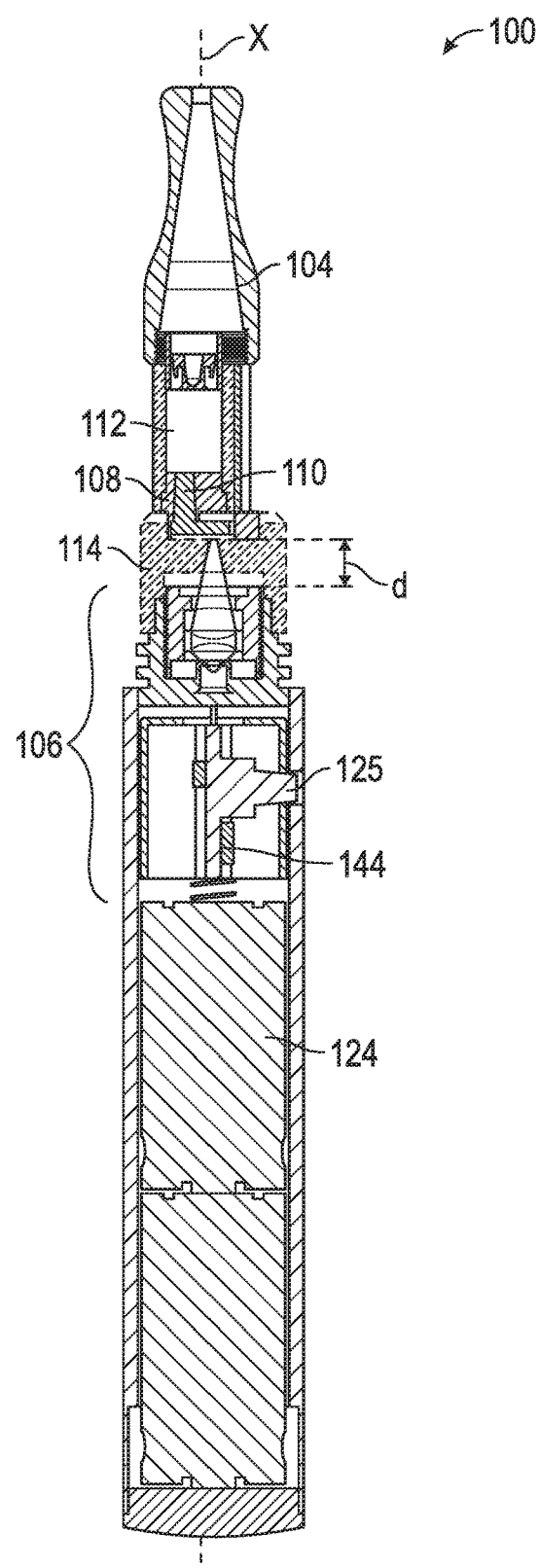
FIG. 4 is another cross-sectional view of the vaporizer of FIG. 1.
Figure 5:
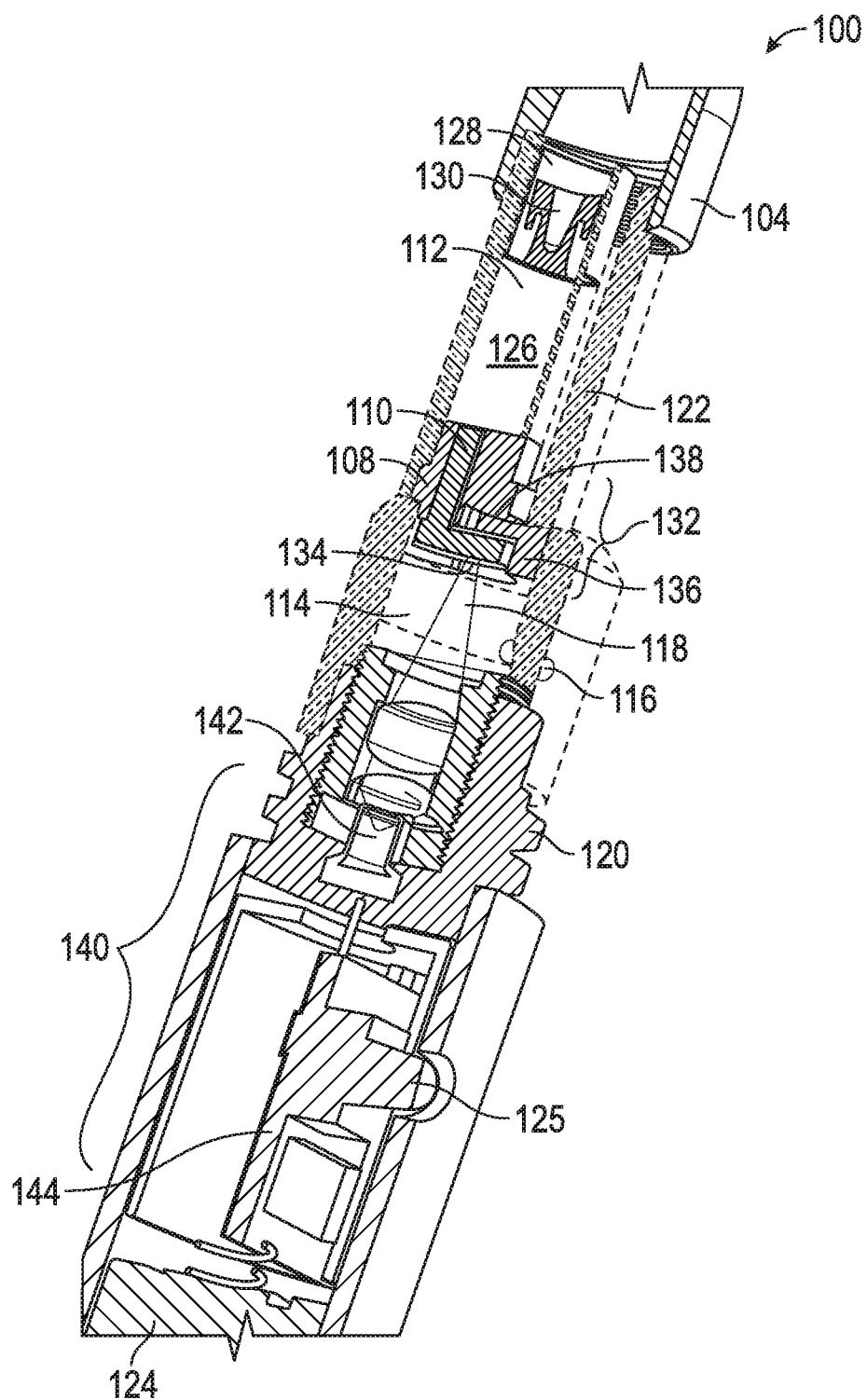
FIG. 5 is a partial cross-sectional perspective view of the vaporizer of FIG. 1.
Figure 6:
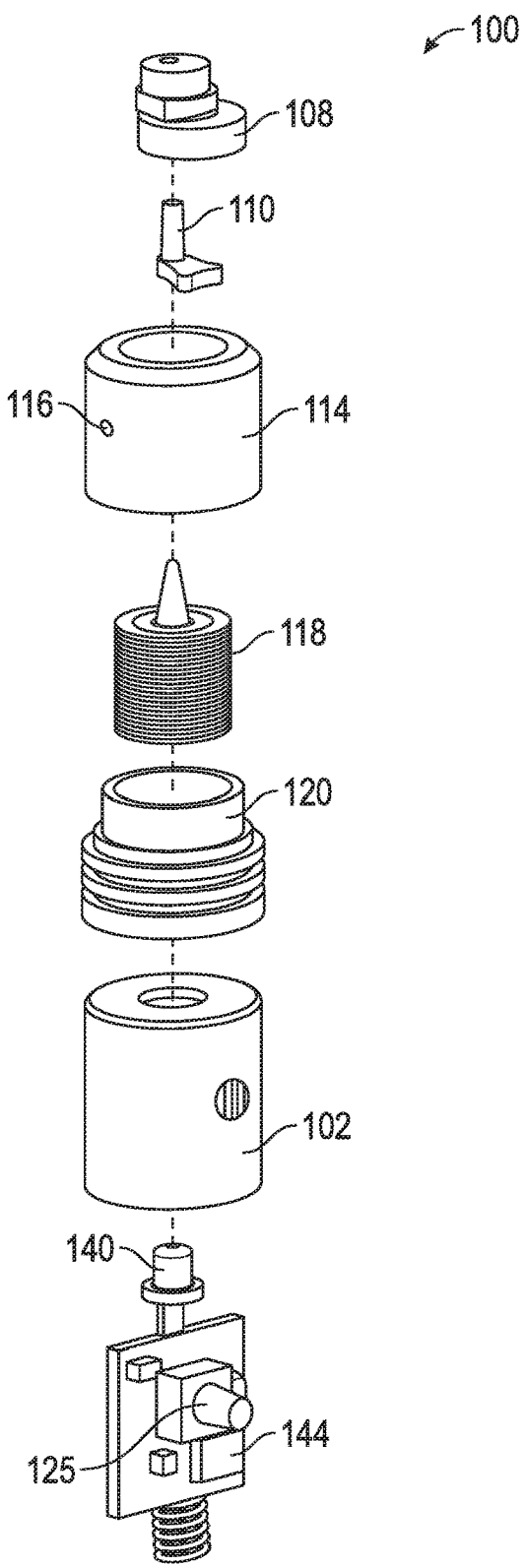
FIG. 6 is an exploded isometric view of one of many embodiments of vaporizer having a laser furnace according to the disclosure.
Figure 7:
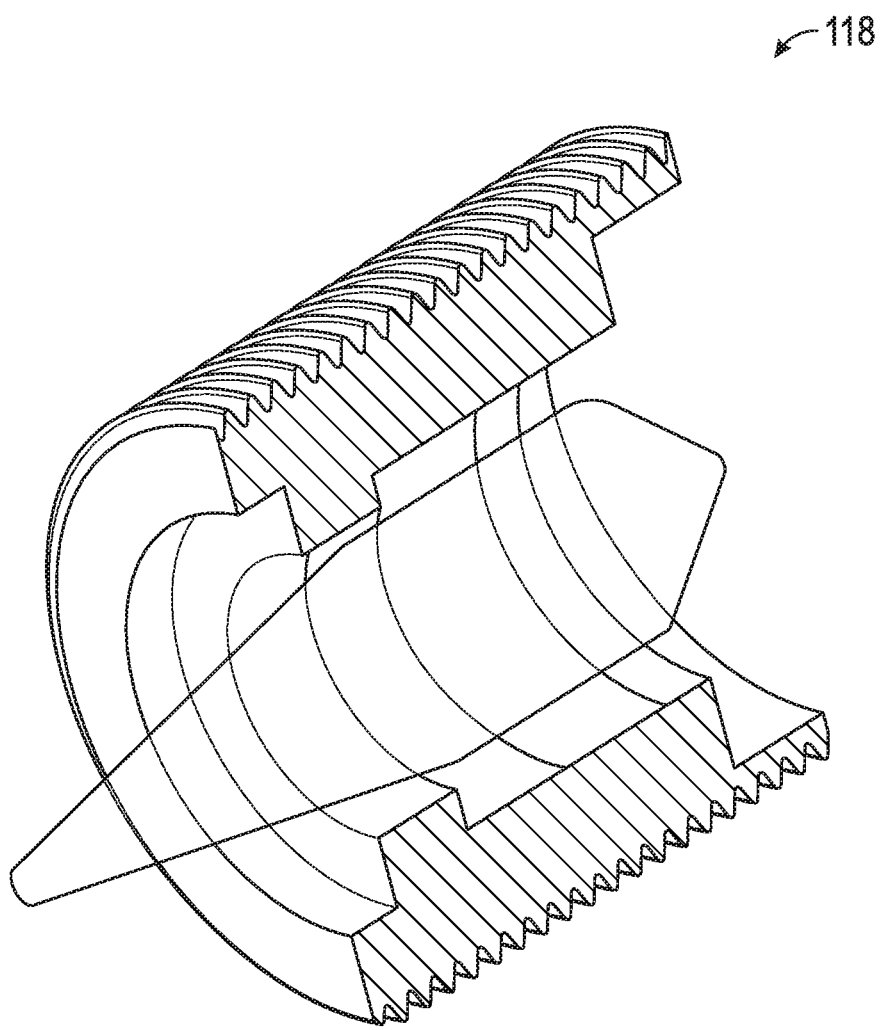
FIG. 7 is a cross-sectional perspective view of one of many embodiments of a lens assembly according to the disclosure.
Figure 8:
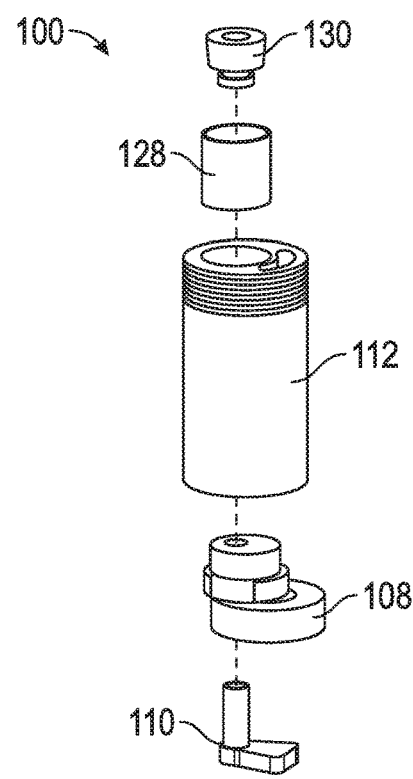
FIG. 8 is an exploded isometric view of one of many embodiments of a feed mechanism according to the disclosure.
Figure 9:
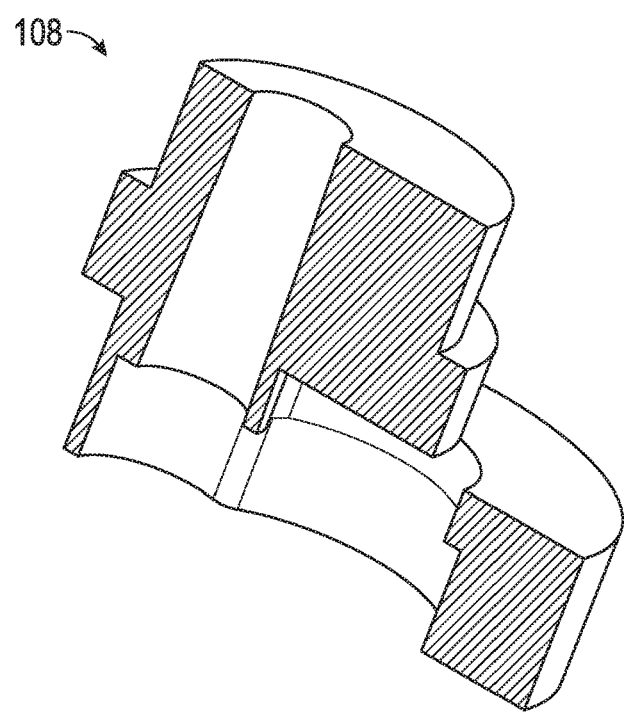
FIG. 9 is a cross-sectional isometric view of one of many embodiments of a feed control mount according to the disclosure.
Figure 10:
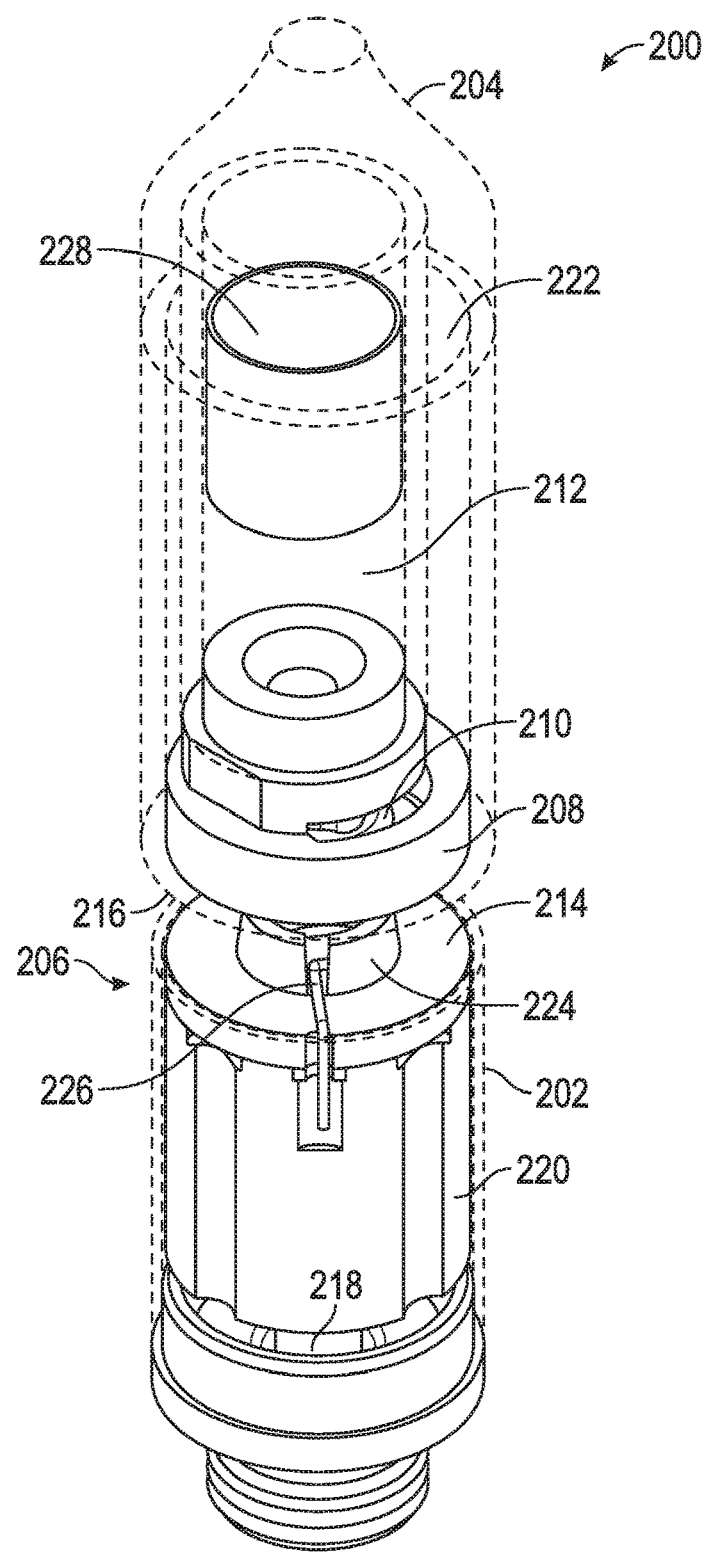
FIG. 10 is an isometric view of another of many embodiments of a vaporizer according to the disclosure.
Figure 11:
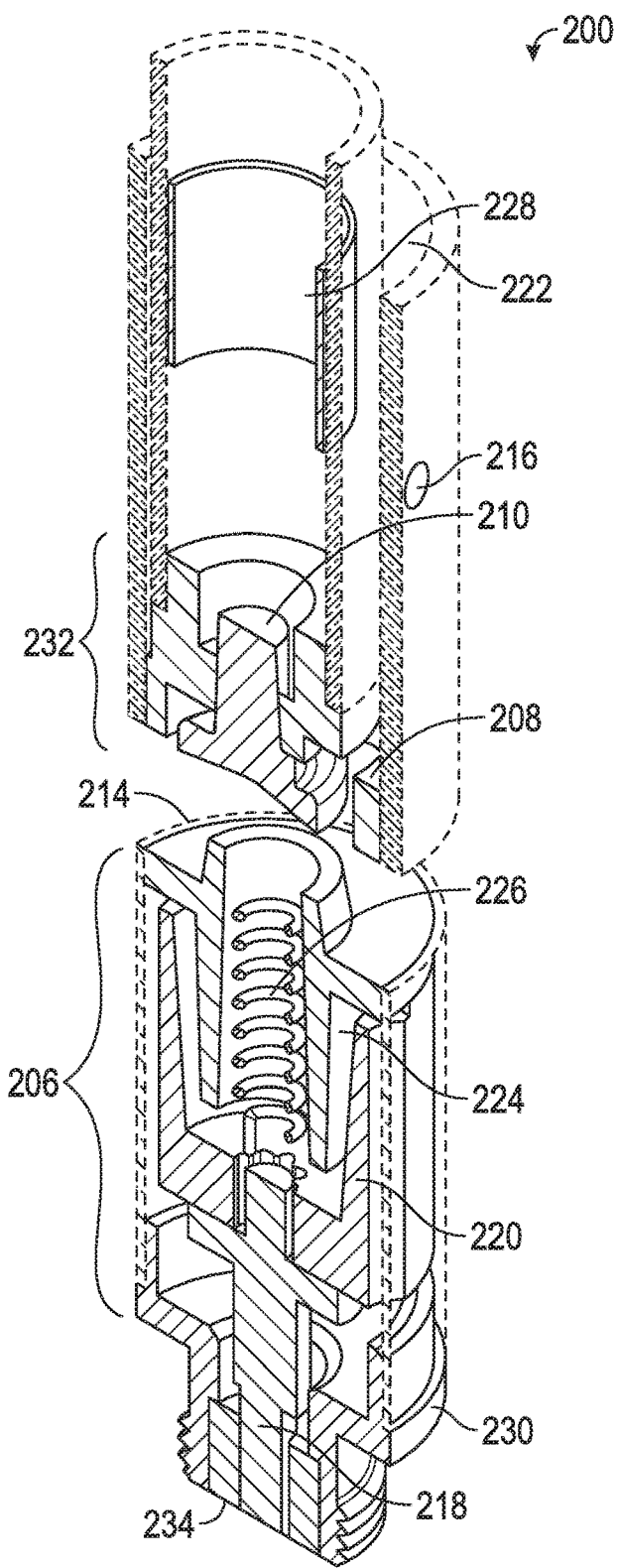
FIG. 11 is a cross-sectional perspective view of the vaporizer of FIG. 10.
Figures 12, 13:
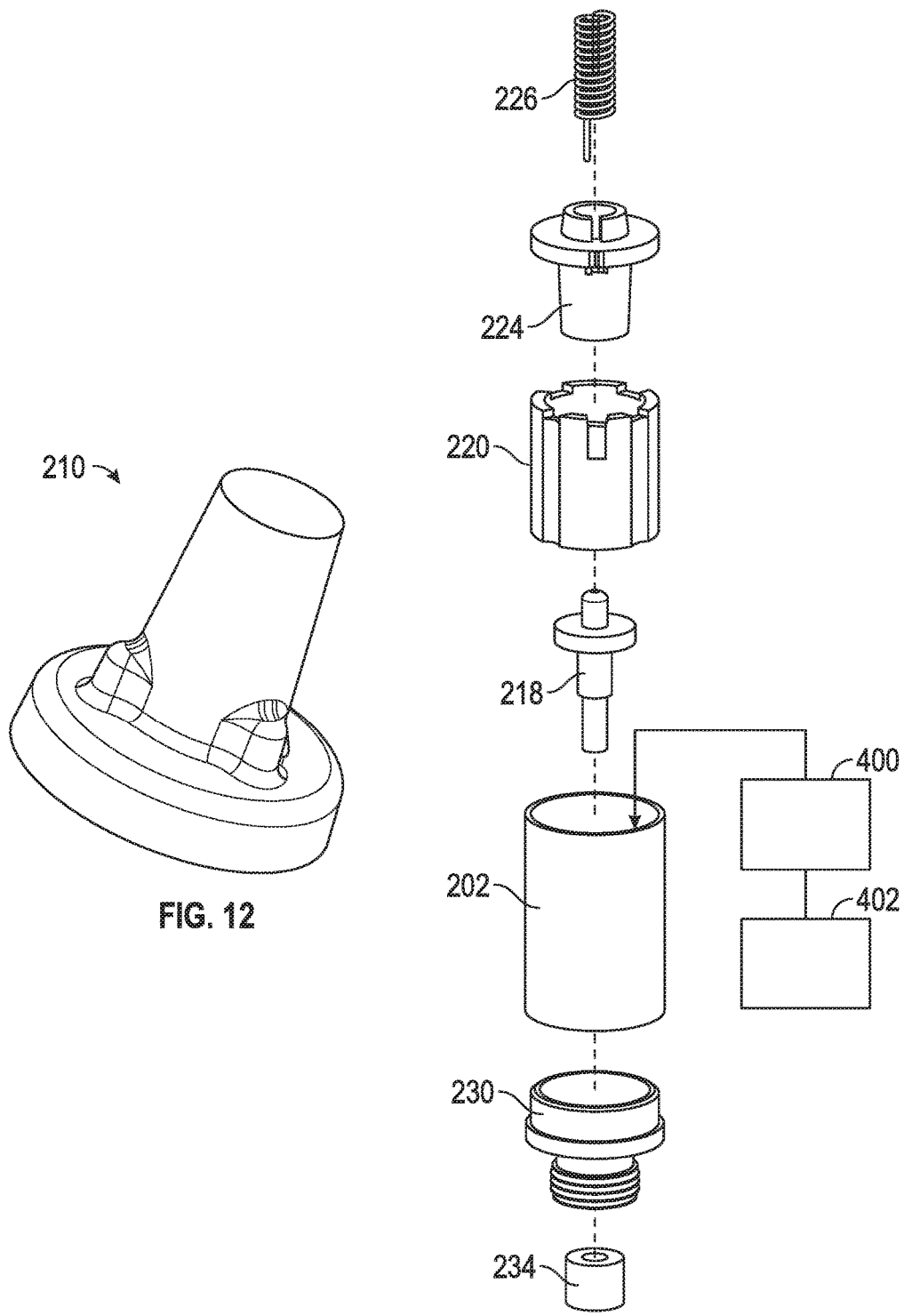
FIG. 12 is a perspective view of one of many embodiments of a feeder according to the disclosure.
FIG. 13 is an exploded isometric view of one of many embodiments of a vaporizer having a tube furnace assembly according to the disclosure.
Figure 14:
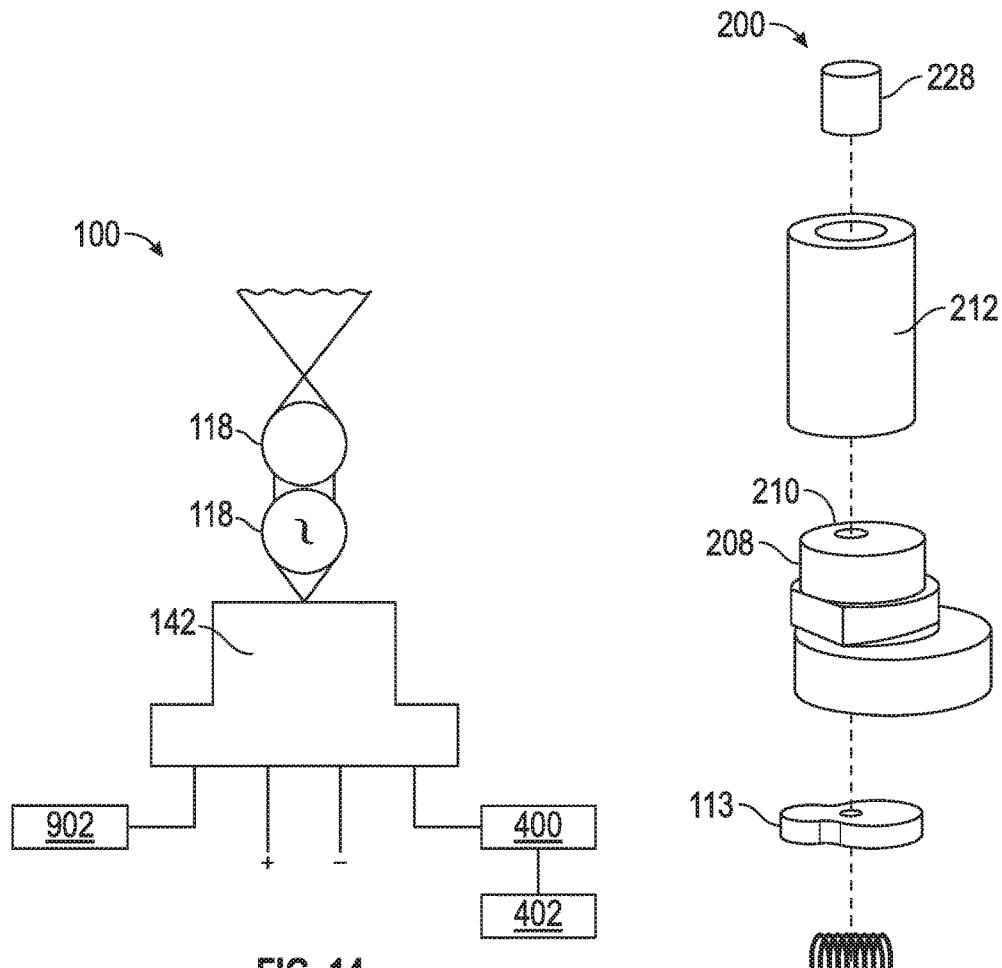
FIG. 14 is a schematic view of another of many embodiments of a vaporizer having a laser furnace according to the disclosure.
Figure 15:
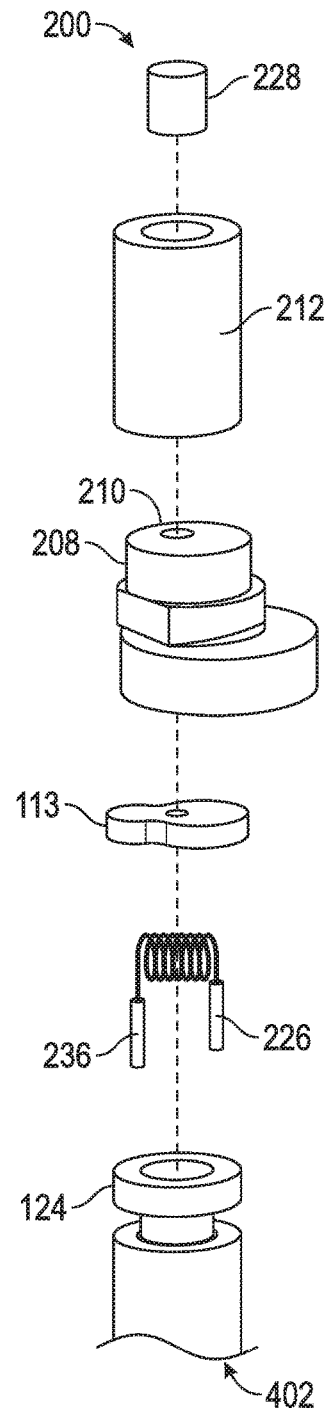
FIG. 15 is an exploded isometric view of one of many embodiments of a vaporizer having a filter according to the disclosure.
Figure 16:
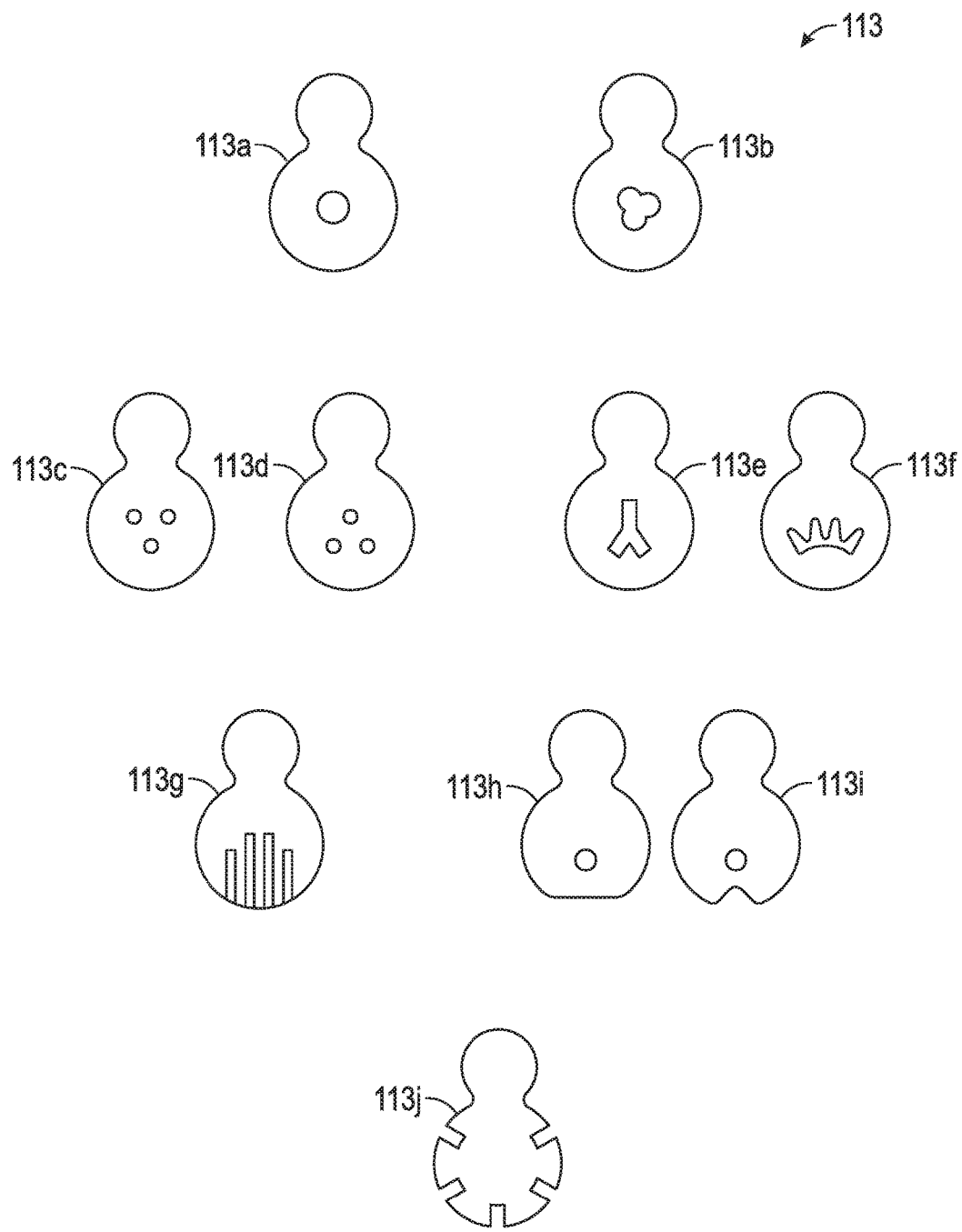
FIG. 16 is a schematic view of some of many embodiments of a filter element according to the disclosure.
Figure 17:
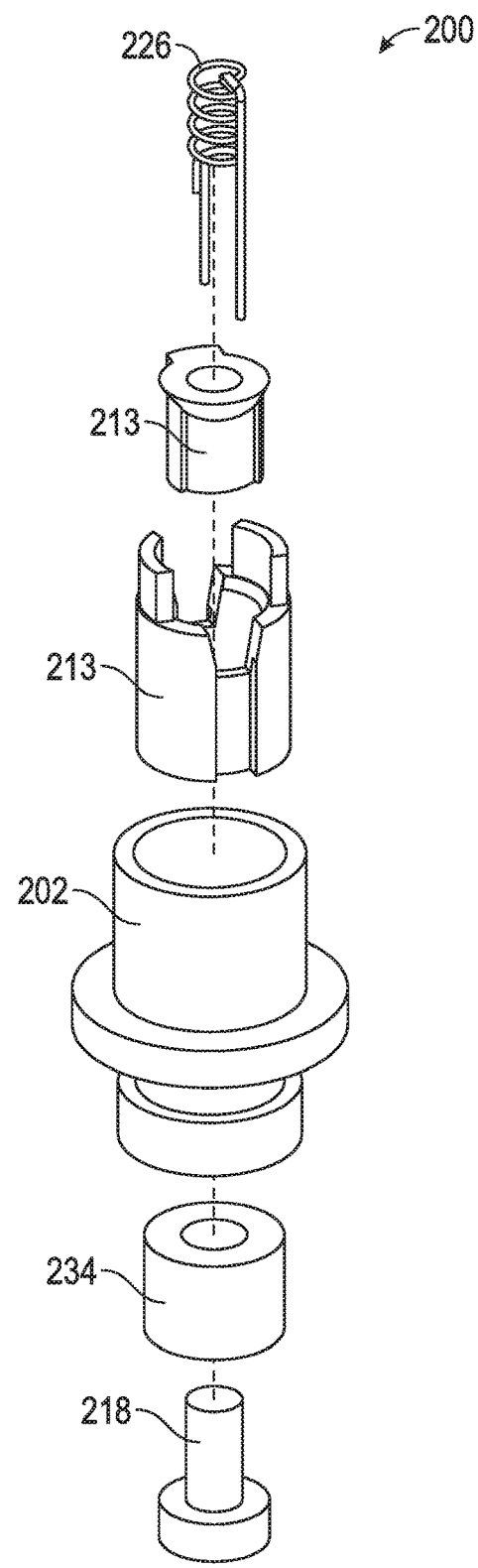
FIG. 17 is an exploded isometric view of one of many embodiments of a vaporizer having a plurality of filters according to the disclosure.
Figure 18:
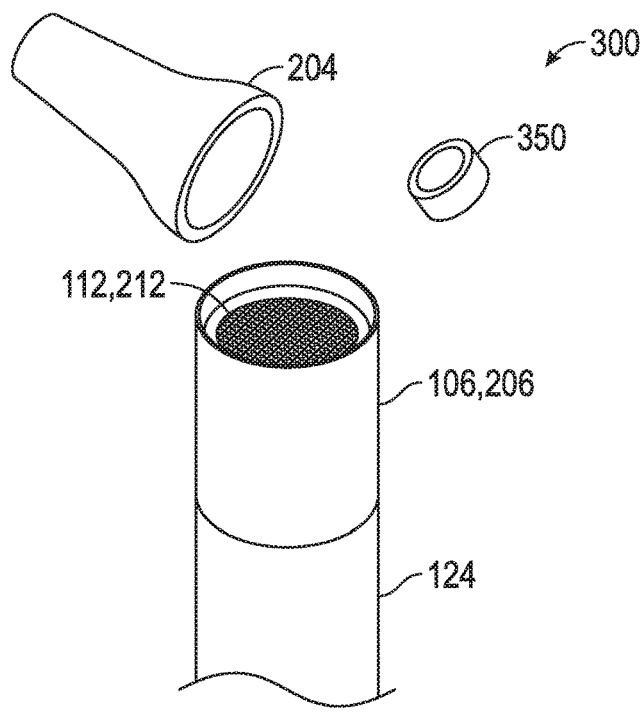
FIG. 18 is an exploded isometric view of one of many embodiments of a vaporizer having a reservoir adapted to couple with one or more tabs according to the disclosure.
Figure 19:
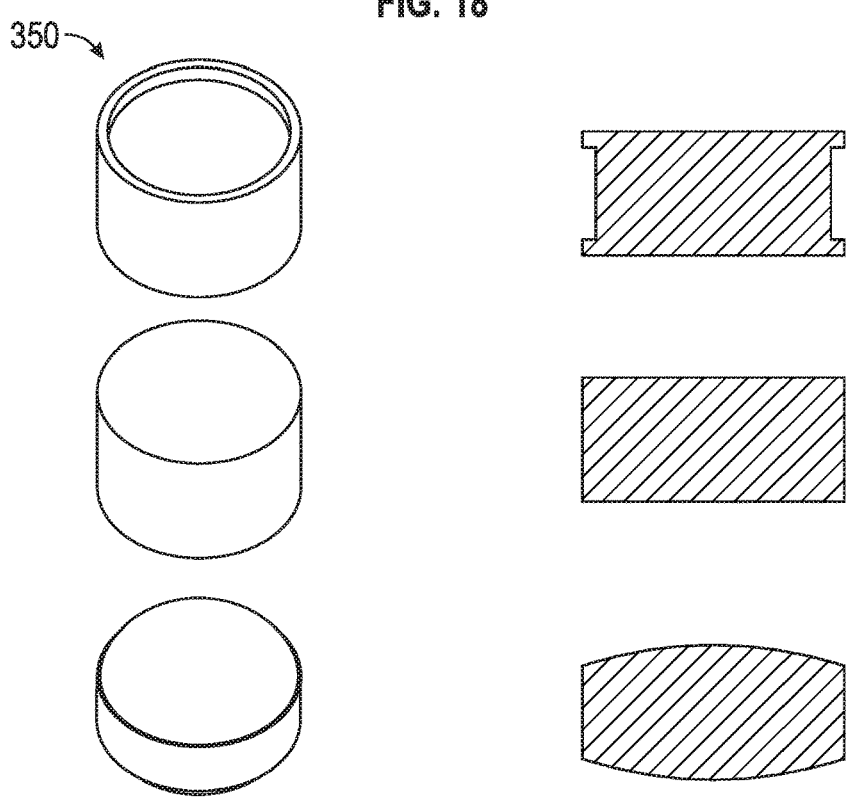
FIG. 19 is a schematic view of some of many embodiments of a tab according to the disclosure.

FIG. 1 is a perspective view of one of many embodiments of a vaporizer according to the disclosure. FIG. 2 is an isometric view of the vaporizer of FIG. 1. FIG. 3 is a cross-sectional perspective view of the vaporizer of FIG. 1. FIG. 4 is another cross-sectional view of the vaporizer of FIG. 1. FIG. 5 is a partial cross-sectional perspective view of the vaporizer of FIG. 1. FIG. 6 is an exploded isometric view of one of many embodiments of vaporizer having a laser furnace according to the disclosure. FIG. 7 is a cross-sectional perspective view of one of many embodiments of a lens assembly according to the disclosure. FIG. 8 is an exploded isometric view of one of many embodiments of a feed mechanism according to the disclosure. FIG. 9 is a cross-sectional isometric view of one of many embodiments of a feed control mount according to the disclosure. FIG. 10 is an isometric view of another of many embodiments of a vaporizer according to the disclosure. FIG. 11 is a cross-sectional perspective view of the vaporizer of FIG. 10. FIG. 12 is a perspective view of one of many embodiments of a feeder according to the disclosure. FIG. 13 is an exploded isometric view of one of many embodiments of a vaporizer having a tube furnace assembly according to the disclosure. FIG. 14 is a schematic view of another of many embodiments of a vaporizer having a laser furnace according to the disclosure. FIG. 15 is an exploded isometric view of one of many embodiments of a vaporizer having a filter according to the disclosure. FIG. 16 is a schematic view of some of many embodiments of a filter element according to the disclosure. FIG. 17 is an exploded isometric view of one of many embodiments of a vaporizer having a plurality of filters according to the disclosure. FIG. 18 is an exploded isometric view of one of many embodiments of a vaporizer having a reservoir adapted to couple with one or more tabs according to the disclosure. FIG. 19 is a schematic view of some of many embodiments of a tab according to the disclosure. FIGS. 1-19 are described in conjunction with one another.

In at least one embodiment, a vaporizer 100, such as a system for vaporizing oil, can include a body 102, such as a housing or cover, for at least partially housing or otherwise supporting one or more other components of vaporizer 100. Vaporizer 100 can include a mouthpiece 104 for routing fluid and communicating with a user's mouth or lips during use of vaporizer 100. For example, mouthpiece 104 can be configured to comfortably or otherwise couple with a user's lips for directing vapor and/or air from within vaporizer 100 or a portion thereof to a user for inhalation. Vaporizer 100 can further include one or more heaters 106 coupled to body 102 for heating at least a portion of oil (not shown) housed within vaporizer 100. Vaporizer 100 can include a feed control mount 108 for holding or otherwise supporting a feeder 110 in fluid communication with one or more other components of vaporizer 100, such as a reservoir 112 for holding or housing oil and a vapor chamber 114 for holding or housing oil vapor. In at least one embodiment, vaporizer 100 can include one or more filters 113 (see, e.g., FIGS. 15-17) for filtering material, such as oil, to be vaporized. Filter 113 can, but need not, be coupled to or part of feeder 110. Vaporizer 100 can include one or more inlets 116, such as an opening or port, for allowing air to flow into or out of one or more components of vaporizer 100, such as vapor chamber 114, and one or more flow passages 122 for routing or otherwise directing fluid flow in or through vaporizer 100 or one or more portions thereof. In at least one embodiment, vaporizer 100 can include one or more power supplies 124, such as a battery or plurality of batteries, for powering heater 106 or one or more other components of vaporizer 100. Vaporizer 100 can include one or more actuators 125, such as a button, switch or other control, for activating and/or deactivating the device, such as by way of controlling electrical or other communication between a power supply 124 and heater 106.

In at least one embodiment, vaporizer 100 can include one or more reservoirs 112, such as a storage space, tank or chamber, for holding oil to be vaporized during use of the vaporizer. Reservoir 112 can have any size, shape, or volume according to a particular application or physical embodiment of the disclosure. In at least one embodiment, which is but one of many, reservoir 112 can have a volume sufficient to hold one gram of oil, but that need not be the case, and reservoir 112 can have a volume for holding more or less than one gram of oil, such as between zero grams and one gram of oil, or more than one gram of oil, such as between one and one hundred grams of oil, or more. In at least one embodiment, which is but one of many, reservoir 112 can be at least generally cylindrical and can have a diameter of about ¼ inch and a length of about 1 inch. However, that need not be the case, and reservoir 112 can have any size or shape, which can include a size based on desired volume or a shape based on compatibility with one or more other components of a physical embodiment of vaporizer 100.

In at least one embodiment, vaporizer 100 can include one or more plugs 128, such as a float or stopper, for supporting the functionality of vaporizer 100, such as by supporting the storage or flow of oil within or through vaporizer 100. Plug 128 can be made from an oil resistant or repellant material (e.g., polycarbonate, rubber, or acetal) and can be configured to float relative to the oil in reservoir 112. For example, plug 128 can be arranged to at least partially float on top of the oil supply, and can have a clearance with an internal surface 126 or wall of reservoir 112 for limiting or preventing the flow of oil past plug 128 in the reservoir. Plug 128 can be adapted to float atop the oil in reservoir 112 and follow the oil level down as the oil supply is depleted during use of vaporizer 100, which can help ensure reservoir 112 is emptied completely or efficiently. Plug 128 can be adapted to function as a fill mechanism, such as an inlet for allowing oil to be added to reservoir 112. For example, plug 128 can be or include a rubber or other elastic portion 130 adapted for allowing a needle to pass there through for injecting oil into the reservoir 112. As another example, plug 128 can include a valve (not shown) or other optionally sealable opening for communicating with the interior of reservoir 112. In at least one embodiment, plug 128 can protect the oil in reservoir from exposure to air or other portions of vaporizer 100. As other examples, plug 128 can be adapted for at least partially preventing bubbles from forming in the oil in reservoir 112 and for keeping the oil in contact with one or more other components (e.g., feeder 110) for supporting proper flow of the oil within vaporizer 100. In at least one embodiment, plug 128 can be adapted for at least partially equalizing or otherwise affecting pressure inside and outside of reservoir, which can also support flow of the oil during use of vaporizer 100.

In at least one embodiment, vaporizer 100 can include a feeder 110, such as a conduit or wick, for feeding oil from one portion of the vaporizer to one or more other portions of the vaporizer, such as from reservoir 112 to a chamber 114, such as a vaporization chamber for supporting vaporization of at least a portion of the oil in vaporizer 100. In at least one embodiment, feeder 110 can be a portion of a feed mechanism 132, or feed assembly, comprising one or more other portions of vaporizer 100, such as one or more of an oil storage reservoir 112, oil or other flow control device such as feeder 110, one or more vapor flow passages 122, such as a flow channel to mouth piece 104, and an oil filling device or inlet such as plug 128 or a portion thereof. In at least one embodiment, feeder 110 can be or include a capillary for feeding oil by way of capillary action, which can help overcome or compensate for changes in the viscosity of the oil within vaporizer 100 due to internal or external temperature changes, such as due to use of the device or during use of the device in different environments. In such an embodiment, feeder 110 can exhibit a capillary action that at least partially reduces or minimizes the time that may elapse during replenishment of a vaporization zone 134 with oil from reservoir 112. In at least one embodiment, feeder 110 can be or include a capillary made from a porous ceramic or sintered metal material, which can have a filter size of, for example, about 30 to about 90 microns, or another filter size according to a particular physical embodiment of the disclosure, which can be any filter size. In at least one embodiment, feeder 110 can be or include a porous ceramic or sintered metal capillary feed device that can be or become low in density and low in mass, which can help minimize an amount of energy sufficient to increase the temperature of the oil to its vaporization point. As another example, feeder 110 can be or include aluminum oxide, which can include aluminum oxide held together with quartz glass or another bonding material or agent. As will be understood by one of ordinary skill having the benefits of the present disclosure, embodiments of the disclosure can be configured for use with one or more types of oil, which can have differing vaporization temperatures, and that material of feeder 110 or a portion thereof can be chosen to facilitate flow and vaporization of oils of different types as needed or desired for a physical embodiment of vaporizer 100.

In at least one embodiment, vaporization chamber 114 can be adapted for supporting vaporization of oil, such as from a liquid or other form to a vapor, which can include a colloidal suspension of droplets in air within or flowing through vaporizer 100 or one or more portions thereof. Chamber 114 can include one or more inlets 116 for allowing airflow into the chamber and one or more outlets 136 for allowing airflow and/or oil vapor out of the chamber. In at least one embodiment, one or more inlets 116 and/or outlets 136 can include a flow control, such as a valve, orifice, or other structure for limiting, directing or otherwise controlling air flow. Chamber 114 can include an inlet 116 or other air intake adapted for controlling flow of vapor or droplets away from a heat source or other component of the vaporizer. For example, inlet 116 can be configured for preventing flow away from a heat source at a rate that can adversely affect vaporization, such as by resulting in too much or too little heating of or vaporization of the oil. In at least one embodiment, chamber 114 can be adapted for keeping oil vapor or droplets from getting into contact with a heat source, such as a heating coil, laser or other heater described elsewhere herein. In at least one embodiment, vaporization chamber 114 can include or be coupled in fluid communication with feeder 110 or feed mechanism 132 for receiving oil from reservoir 112 for vaporization. In at least one embodiment, vaporizer 100 can be adapted for routing oil vapor (or other vapor, e.g., if a substance other than oil is used or present) to or though one or more air channels or passages (such as flow passage 122) within or through vaporizer 100 without being forced or otherwise routed too close to a heat source (further described below), which can include having a feeder 110, feed mechanism 132 or other portion of vaporizer 100 shaped and arranged for directing vapor away from such heat source during use of vaporizer 100. For instance, vapor can be routed to mouthpiece 104 via flow passage 122 in a direction longitudinally opposite of vaporization zone 134 or a heat source along central longitudinal axis X of vaporizer 100. In at least one embodiment, vaporizer 100 can be adapted for collecting or controlling condensate within a portion of the vaporizer (e.g., condensation due to temperature change), which can include routing or recycling of oil condensate to or back to feeder 110, such as a capillary or other feed mechanism described herein, via one or more flow paths, such as return passage 138.

In at least one embodiment, vaporizer 100 can at least partially prevent or minimize burning of oil by preventing oil from coming into direct contact with a heat source, such as heater 106 or heater 206 (further described below). For example, oil can be held in place by capillary action of feeder 110. Further, flow and/or flow rate of the oil can be controlled by capillary action of feeder 110. Such holding and control of the oil can be accomplished or affected by, for example, the material type or density of feeder 110. Carbonization of the oil can be prevented or minimized by preventing oil from coming into contact with a heat source, which can include disposing oil for heating within at least a portion of feeder 110 and disposing feeder 110 or vaporization zone 134 distally from the heat source, such as a distance d across vaporization chamber 114, which can be any distance according to a physical embodiment of the disclosure. In at least one embodiment, distance d can be a distance sufficient to at least partially minimize carbonization or the potential for carbonization of the oil while nonetheless being small enough for facilitating adequate heating of the oil for vaporization.

In at least one embodiment, vaporizer 100 can be adapted for at least partially preventing or minimizing leaking of oil, such as by controlling or limiting the flow of oil in or through feeder 110. Oil can be prevented from leaking from feeder 110 due to the energy needed to separate the oil from the feeder or a portion thereof. In at least one embodiment, leaking can be at least partially prevented by plug 128 (which can include portion 130 thereof), which can be floating on top of oil in reservoir 112 and which can prevent bubbling of the oil and bias the oil in contact with feeder 110 (and/or feed control mount 108) or a portion thereof, which can be or include a wicking feed material such as one or more of those described elsewhere herein. In at least one embodiment, leaking can be at least partially prevented by preventing at least a portion of plug 128 from sinking into the oil. For example, plug 128 can be coupled to reservoir 112 so that plug 128 follows the oil level down (with reference to the orientation shown in the Figures, although it could be another direction, such as up) as oil is removed from reservoir 112 during use of vaporizer 100 by a user while also being at least partially prevented or otherwise kept from moving into the oil or more than a distance into the oil. In at least one embodiment, plug 128 can be configured to at least partially float on or in oil within reservoir 112. In at least one embodiment, plug 128 can be configured to at least partially resist movement in a direction toward oil in reservoir 112, such as by being coupled with reservoir 112 by friction fit, interference fit, or the like.

In at least one embodiment, vaporizer 100 can at least partially prevent or minimize clogging of one or more passages or conduits, such as flow passage 122, by minimizing the exposure of oil in reservoir 112 to air, including by way of plug 128, and by way of minimizing the potential for evaporation of the oil within vaporizer 100. For example, plug 128 can be sealingly coupled to reservoir 112 for minimizing air ingress into reservoir 112. Clogging of one or more air intake openings or vents, such as inlet 116, can be prevented by minimizing the escape of oil from feeder 110 or a portion thereof, such as a ceramic or other feed structure. Loss of oils due to not being able to get the oils to flow, i.e., due to partial or complete inoperation of vaporizer 100 after some amount of use by a user, can also be minimized or prevented. Feeder 110 can be made at least partially from a porous ceramic, sintered metal or other material that can hold up to the PH levels of the oil, which can at least partially prevent or reduce the chance of experiencing a metallic taste or flavor during use of the device. Exemplary ceramic materials can include aluminum oxide and silicon carbide. Exemplary sintered metal materials can include passivated stainless steel and phosphor bronze.

In at least one embodiment, vaporizer 100 can include one or more heaters 106 for heating oil during use, such as by heating at least a portion of oil to a vaporization point or vaporization temperature. The vaporization temperature can depend on the oil or oils used in vaporizer 100. For example, in at least one embodiment, heater 106 can heat oil to a temperature of from about 270 degrees Fahrenheit to about 360 degrees Fahrenheit, or another temperature sufficient to vaporize at least a portion of the oil, which can be any temperature according to a particular application or oil used therefor. As noted above, in at least one embodiment, vaporizer 100 can be adapted to segregate or distance heater 106 and the oil for at least partially preventing direct contact between heater 106 and the oil, for instance, to prevent or minimize overheating, burning or carbonization of the oil. In at least one embodiment, vaporizer 100 can be adapted to vaporize at least a portion of oil stored therein at a temperature of less than 375 degrees Fahrenheit. In at least one embodiment, vaporizer 100 can be adapted to heat at least a portion of oil stored therein to a temperature for supporting flow of oil within vaporizer 100 or a portion thereof, such as through feeder 110, which can include, for example, heating oil to about 160 degrees Fahrenheit or another temperature between an ambient temperature and a burning or carbonization temperature of the oil. Vaporizer 100 can be adapted to vaporize oil disposed in vaporization zone 134, which can include heating at least a portion of feeder 110.

As shown, for example, in FIGS. 1-6, heater 106 can be or include a laser heater and can include one or more lasers 140 for heating the oil, such as a laser for converting electrical energy into light and/or heat adapted to heat the oil, which can include a beam directed at or onto at least a portion of feeder 110. Such an embodiment of heater 106 can be referred to as a laser furnace and can include various components for supporting operation of laser 140, such as, for example, one or more heat sinks 120, one or more diodes 142, laser control electronics 144, and the like. In at least one embodiment, vaporizer 100 can be adapted to heat oil with laser 140 by heating feeder 110 or filter 113 (if present). Laser temperature can be controlled in one or more of at least two ways, separately or in combination, in whole or in part. For example, the power applied to laser 140 can be varied for controlling the temperature of laser light directed to feeder 110 or otherwise directed within vaporizer 100 for heating the oil. As another example, the amount of heat applied to feeder 110 or otherwise directed within vaporizer 100 for heating the oil can be controlled by way of Pulse Width Modulation (PWM), or the high speed switching of the laser on and off. In at least one embodiment, PWM control can allow for a laser, such as, for example, a 1.6 watt or 2.2 watt laser, to energize the oil to a vapor state quickly, which can include instantaneously or about instantaneously upon application of the laser light to the oil or another portion of vaporizer 100 for heating the oil. In at least one embodiment, vaporizer 100 can include a laser 140 that operates at a resonant frequency of from about 40 hertz to about 50 hertz and a duty cycle of about 20% to about 30%. In at least one embodiment, the time to vaporization can depend on the time elapsed between activation(s) of heater 106, laser 140 or vaporizer 100, which can affect the temperature of the oil at the time of an activation, separately or in combination with other factors, such as, for example, the ambient temperature in the location of use. Additionally, or individually, PWM can allow for control of the length of time for which laser 140 is activated or applied during use and for control of the activation time sufficiently to prevent burning of the oil due to overheating. In at least one embodiment, laser 140 can be adapted to concentrate the application of heat to the oil for reducing the vapor droplet size relative to one or more other embodiments of heat sources described herein. In at least one embodiment, a heater 106 having a laser 140 can reduce the power consumption for heating the oil relative to one or more other embodiments of heater 106 or vaporizer 100 (200, etc.). Laser light can be concentrated on one or more locations, such as a focus point or focal point, which can include controlling the light with or otherwise passing the light through one or more lenses 118, for heating the oil, which can, in at least one embodiment, result in less power consumption for heating the oil to a temperature (which can be any temperature) versus the power consumption of a heating coil for heating the oil to that temperature. For example, a heating coil (further described below) can heat some or all of vaporization chamber 114 and/or feeder 110 prior to oil vaporization taking place. Lens 118 can be or include one or more convex lenses, concave lenses, ball lenses, or other lenses, separately or in combination, in whole or in part. In at least one embodiment, a laser light frequency of laser 140 can be selected in consideration of the thermal absorption characteristics of feeder 110, feed mechanism 132, one or more oils used with vaporizer 100, or one or more other components of vaporizer 100, separately or in combination, in whole or in part. In at least one embodiment, vaporizer 100 can include a laser 140 having a light frequency of, for example, about 435 or 445 nanometers (blue); however, other light frequencies are possible, which can include any light frequency according to a particular application or physical embodiment of the disclosure (e.g., greater than or less than 445 nanometers).

In at least one embodiment, laser 140 can produce a concentrated and controllable heat source that can be directed to a capillary feeder, such as feeder 110, or other portion of feed mechanism 132 for efficiently heating oil in the vaporizer, such as in vaporization zone 134. Temperature can be controlled by controlling the on/off time of the laser light, which can be controlled as a percentage of laser activation time. Temperature can be controlled by controlling the voltage and/or current to laser 140, such as for setting thermal heating of one or more localized areas on the feeder or elsewhere within the vaporizer (e.g., vaporization zone 134) for heating at least a portion of the oil therein. Power consumption can be minimized through localized thermal heating with laser 140. The power consumption of the laser diode 142 and laser control electronics 144 of laser 140 can be less than the power consumption of one or more other types of heat sources, such as a heating coil. In at least one embodiment, vapor droplet size can be reduced (versus one or more other heat sources) by laser heating of the oil, such as due to the localized heating on feed mechanism 132 or another component of vaporizer 100, such as feeder 110. A reduction of droplet size can help prevent condensation of oil within vaporizer 100. In at least one embodiment, vaporizer 100 can include a laser 140 having a laser temperature configured to reduce or avoid burning or carbonization of the oil. In at least one embodiment, laser 140 can have an adjustable focus point, which can include by way of one or more lenses 118. In at least one embodiment, laser 140 can have a set focus point and can be adapted to be defocused for achieving oil vaporization, which can help avoid or prevent burning and carbonization of oil. In at least one embodiment, vaporizer 100 can include one or more safety interlocks or other safety features for at least partially minimizing the risk of damage to a user's eyes or otherwise, such as, for example, focus or defocus features. In at least one embodiment, for example, laser 140 can include a focus point set for preventing damage to a user's eyes in the event one or more other safety features fails. For instance, while the focal point of laser 140 can be of a relatively hot temperature (e.g., 550 degrees Fahrenheit), the focal point can be configured so that the light from laser 140 is diffused enough over a relatively short distance (e.g., a distance from vaporization zone 134 to mouthpiece 104) to minimize or prevent damage to a user's eye. As another example, vaporizer 100 or one or more portions thereof (e.g., body 102, reservoir 112, or chamber 114) can be configured for preventing light from laser 140 from being viewed by a user (at least absent disassembly of the device) or limiting or controlling any viewable light so as to avoid or minimize any potential for harm to a user's eyes.

With continuing reference to the remaining Figures, and specific reference to, for example, FIGS. 10-13, one or more other embodiments of a vaporizer according to the disclosure will now be described. In at least one embodiment, a vaporizer 200 can include a body 202, a mouthpiece 204, a heater 206, a feed control mount 208, a feeder 210, a reservoir 212, a vapor chamber 214, which can include an inlet 216, a flow passage 222 and a plug 228. Vaporizer 200 and the foregoing components can generally function in the manner described above with regard to vaporizer 100 and such similarities need not be repeated or described again here. However, vaporizer 200 can differ in one or more respects. For example, in at least one embodiment, heater 206 can differ from heater 106 in that, rather than (or collectively with) including a laser 140, heater 206 can be or include one or more other heat sources, such as one or more resistance heating elements 226 ("coil 226"), such as a wire, coil or other conductor, for converting electrical energy into heat and heating oil within vaporizer 200. In such an embodiment, which is but one of many, vaporizer 200 can include one or more components for supporting coil 226. For instance, vaporizer 200 can include one or more conductors 218 for electrically coupling coil 226 to one or more power sources, such as a battery or battery pack (see, e.g., power supply 124). Vaporizer 200 can include a base 220 and top 224 for holding or otherwise supporting coil 226, such as within or otherwise relative to body 202. Top 224 can be configured to couple with one or more other components of vaporizer 200, such as reservoir 212 or feed control mount 208, for disposing coil 226 in one or more positions relative to feeder 210 for heating oil within vaporizer 200. In at least one embodiment, vaporizer 200 can include one or more couplers 230 for coupling with a power supply, such as by way of a threaded connection or otherwise, and can include one or more guides 234 for supporting alignment or electrical communication between a power supply coupled to coupler 230 and one or more other components of vaporizer 200, such as conductor 218 or coil 226. In at least one embodiment, heater 206 can be adapted to heat oil to a vaporization temperature within about 2 seconds of activation of vaporizer 200 or, as other examples, in less than 2 seconds or more than 2 seconds from activation.

In at least one embodiment, heater 206 can be or include an exposed coil for applying heat to oil, such as by conductively or radiantly heating feeder 210 or at least a portion of a feed mechanism 232, which can include one or more filters 213 (if present). In such an embodiment, which is but one of many, vaporizer 200 can include a radiant thermally reflective or refractive material 236 (e.g., aluminum foil, ceramic, fiberglass) positioned behind or otherwise relative to coil 226 for directing heat toward feeder 210 or another portion of the vaporizer for heating the oil therein. The temperature of heater 206 or the oil can be controlled, for example, by controlling the voltage or current supplied to the heater 206. In at least one embodiment, vaporizer 100, 200 can include a plurality of filters 113, 213 (see FIG. 17), which can include filters of the same or different densities or porosities. Filters 113, 213 can be of any size and shape according to a physical embodiment of the disclosure, and can have any number, size and shape of openings, such as round, clover, slotted, sliced, rectangular or other holes or fluid paths. A number of configurations for a filter 113, 213 are shown in FIG. 16 for illustrative purposes (labeled 113*a*, 113*b*, etc., for purposes of convenience of reference) although it should be understood that such examples are not limiting and that other shapes, sizes and configurations of a filter 113, 213 are possible.

In at least one embodiment, heater 206 can include an at least partially enclosed coil 226, such as a coil or other element at least partially contained within a tube or other enclosure (e.g., base 220 and/or top 224), for producing heated air flow routed across or directed to feeder 210 or another portion of vaporizer for heating the oil therein. Such an embodiment of heater 206 can be referred to as a tube furnace. Radiant thermal energy can be reflected by refractory ceramic or another material (not shown) for increasing thermal content of the air flow. Similarly, the temperature of heater 206 or the oil can be controlled, for example, by controlling the voltage or current supplied to the heater. Burning or carbonization can be at least partially prevented or minimized by preventing the oil from coming in contact with heater 206 or coil 226, or by controlling the air supply through at least a portion of the device, which can include controlling the power directed to one or more coils 226 or other heat sources. Heating of feeder 210 or feed mechanism 232, such as one disposed at least partially within a vaporizing chamber 214, can include reflecting radiant heat energy from a heat source, such as a nickel chrome or other heating coil 226, toward feeder 210, such as a capillary feed or other feed. Radiant heat can be directed toward feeder 210 or the oil, which can include coupling a ceramic or other material having refractive qualities and/or a thermal radiant reflective material in or to at least a portion of vaporizer 200, such as to or near heater 206 or another portion of vaporizer 200.

As shown and described above with reference to vaporizers 100, 200, reservoirs 112, 212 can be configured for storing oil in liquid form and feeders 110, 210 and/or filters 113, 213 can be configured for moving oil from reservoirs 112, 212, such as by wicking or capillary action, to an area of vaporizer 100, 200 for heating or vaporization (e.g., vaporization zone 134). However, this need not be the case, and other embodiments of vaporizers according to the disclosure exist. In at least one embodiment, a vaporizer 300 can be adapted to vaporize oil that is stored in a form other than liquid residing in a reservoir, which can include being adapted to receive or otherwise couple with one or more tabs 350, such as a tablet, cylinder, or disk, comprising the oil. A tab 350 according to the disclosure can include, for example, a piece of porous ceramic or sintered metal (such as those materials described elsewhere herein) soaked, injected or infused with oil, such as to the point that the oil is held in place by capillary action or is otherwise resistant to being removed or rubbed off from tab 350 by touch. In such an embodiment, which is but one of many, a vaporizer can include a reservoir 312 configured for holding one or more tabs 350 and for supporting the tab(s) during heating. In at least one embodiment, a reservoir 312 for tabs can serve as an alternative to a reservoir with a wicking feed or other feed as described herein, but that need not be the case and, in at least one embodiment, one or more of such reservoirs and corresponding components can exist collectively. Tab 350 can, but need not, take place of or be substituted for one or more other components of a vaporizer, such as one or more of a feeder (e.g., feeders 110, 210) or filter (e.g., filters 113, 213), in whole or in part.

In at least one embodiment, tab 350 can include a relatively limited number of doses relative to a liquid reservoir embodiment, such as one, two, three, or up to fifty doses, and can be disposable and/or replaceable after use. Tab 350 can provide a convenient and clean way for users to transport or store oil for use in a vaporizer. A vaporizer configured for coupling with one or more tabs 350 can include one or more heat sources for heating one or more tabs 350 to vaporize at least a portion of the oil in the tab(s) during use, such as one or more of heaters 106, 206 described elsewhere herein. As another example, a vaporizer can include a nail heating device, which can include a chamber heated by a torch, flame, or other heat source that heats the nail to a high enough temperature for causing vaporization of the oil, yet, in at least one embodiment, to a temperature below a carbonizing or burning temperature of the oil. Tab 350 can be adapted to have a thermal mass for providing enough heat energy to vaporize at least a portion of the oil content of the tab. A vaporizer can at least partially prevent or minimize carbonization or burning of the oil, such as by preventing the oil from coming into direct or other contact with a heating coil or other heat source. Oil can be held in place on or within a tab 350 by capillary action or another manner according to a particular application or physical embodiment of the disclosure. Oil can be vaporized by applying heat to or otherwise heating tab 350. In at least one embodiment, tab can have a mass that reduces or minimizes an amount of energy needed to heat the tab or to heat at least a portion of the oil coupled to the tab to a vaporization point. Tab 350 can have any size or shape according to a physical embodiment of the disclosure. For example, tab 350 can be disk-shaped, which can, but need not, include having a raised border or other portion, such as for surrounding a logo formed or printed on one or more sides of tab 350. As other examples, tab 350 can be pill-shaped, or another shape, such as square, cubical, pentagonal, hexagonal, octanol, oblong, or any other shape for coupling with a reservoir 312 adapted to couple with one or more tabs 350.

Figure 20:
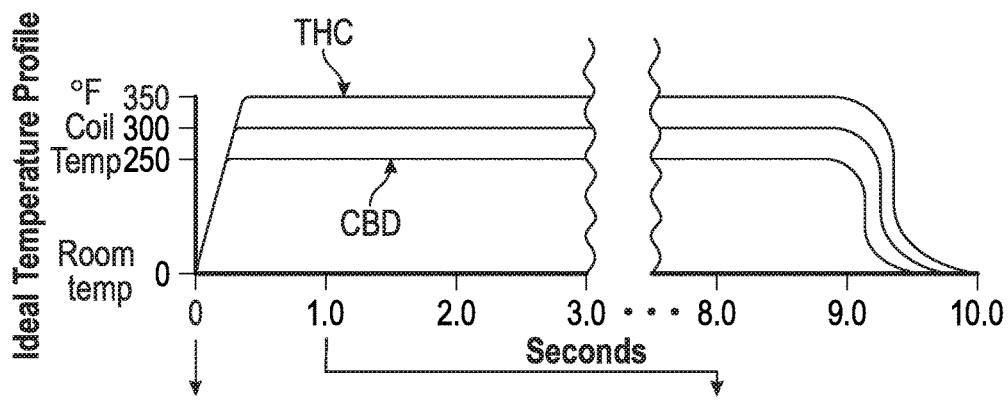
FIG. 20 is one of many embodiments of an ideal temperature profile for vaporization of an oil according to the disclosure.
Figure 21:
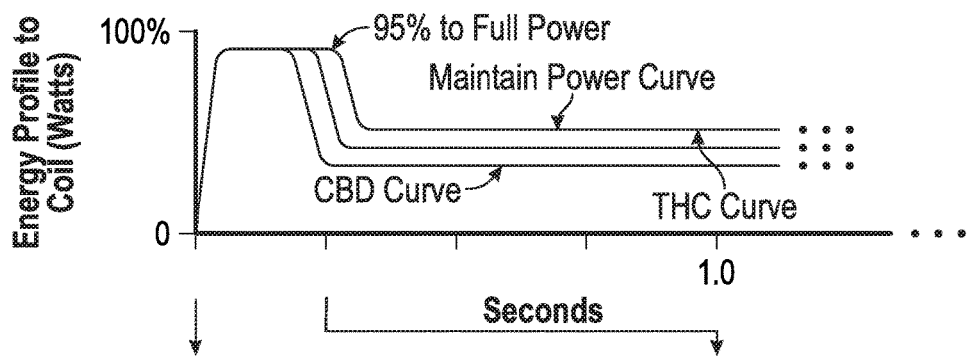
FIG. 21 is one of many embodiments of an energy profile sent to a coil according to the disclosure.
Figure 22:
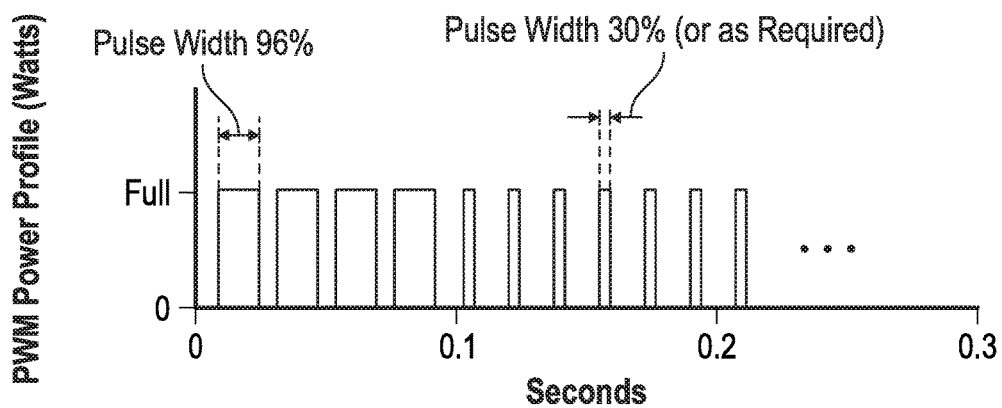
FIG. 22 is one of many embodiments of a PWM profile output for delivering power to a coil according to the disclosure.
Figure 23:
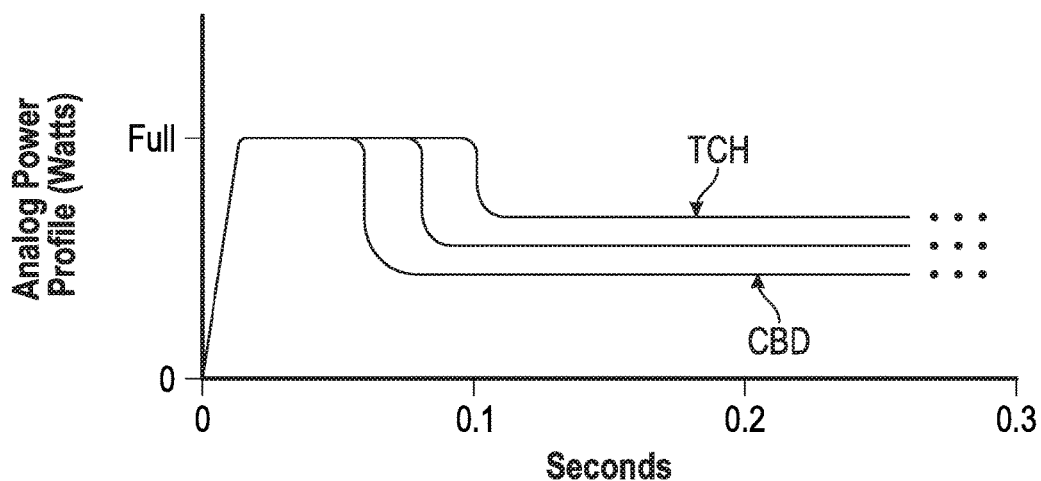
FIG. 23 is one of many embodiments of an analog equivalent of a PWM profile according to the disclosure.
Figure 24:
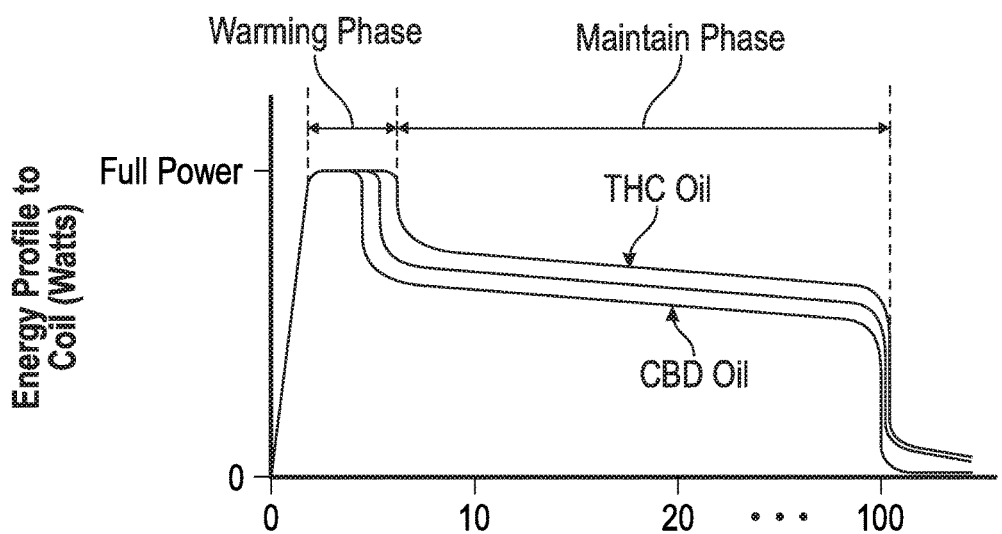
FIG. 24 is one of many embodiments of an expanded power profile to a coil according to the disclosure.
Figure 25:
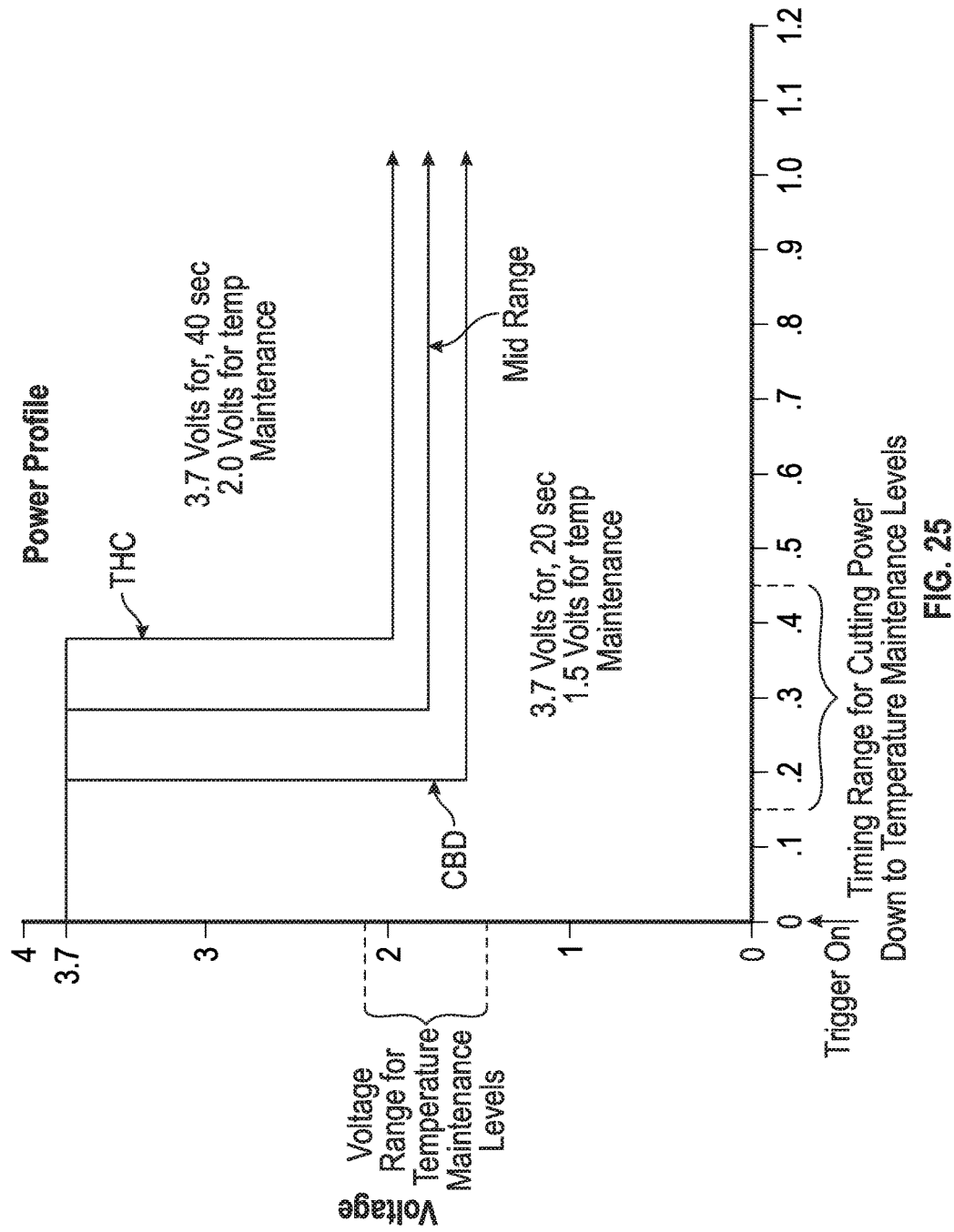
FIG. 25 is yet another of many embodiments of a power profile for vaporization of an oil according to the disclosure.
Figure 26:
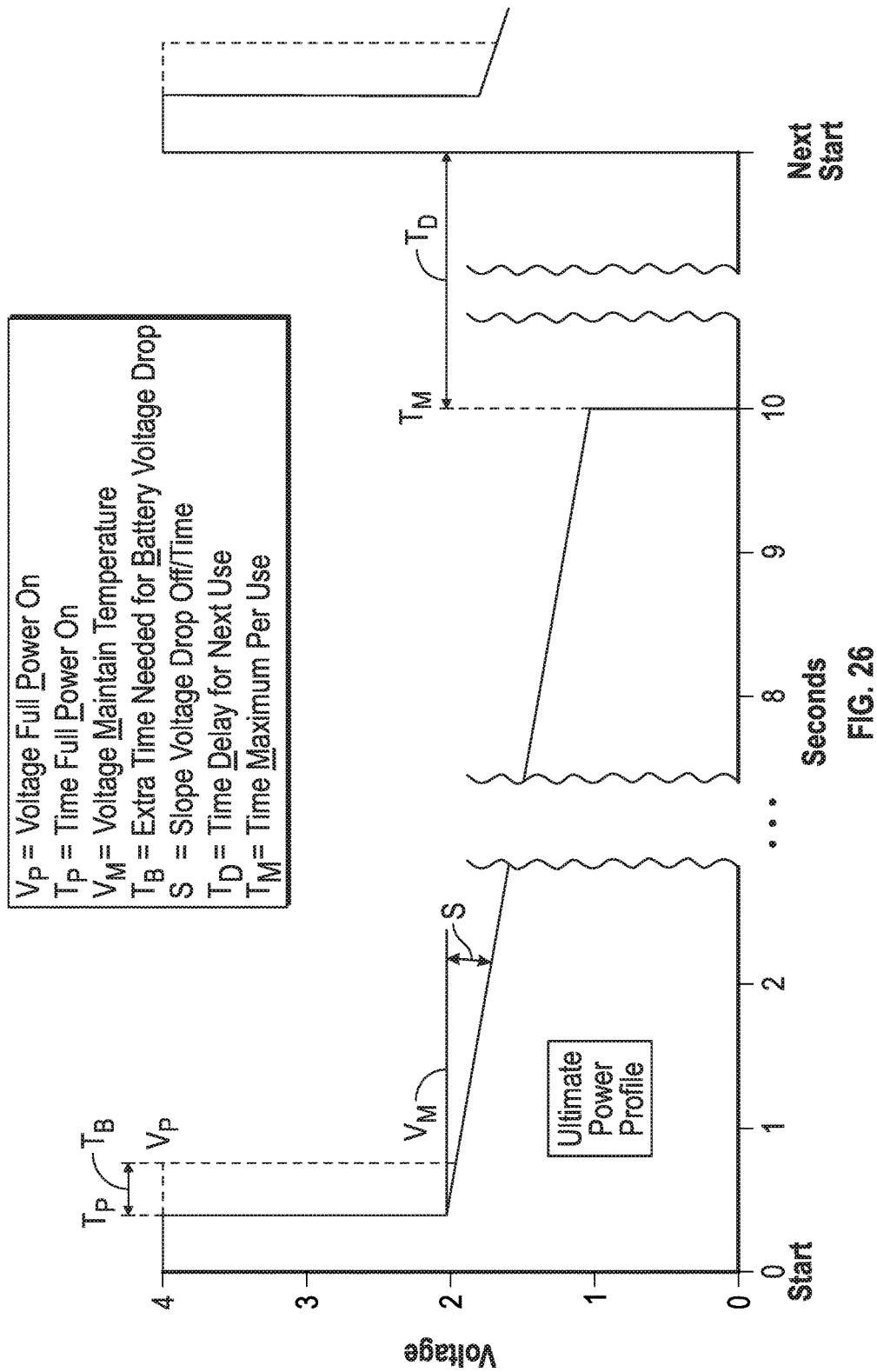
FIG. 26 is yet another of many embodiments of a power profile for vaporization of an oil according to the disclosure.

FIG. 20 is one of many embodiments of an ideal temperature profile for vaporization of an oil according to the disclosure. FIG. 21 is one of many embodiments of an energy profile sent to a coil according to the disclosure. FIG. 22 is one of many embodiments of a PWM profile output for delivering power to a coil according to the disclosure. FIG. 23 is one of many embodiments of an analog equivalent of a PWM profile according to the disclosure. FIG. 24 is one of many embodiments of an expanded power profile to a coil according to the disclosure, which can include a sloped power profile, such as for maintaining of a temperature as a wick is increasing in temperature over time. FIG. 25 is yet another of many embodiments of a power profile for vaporization of an oil according to the disclosure. FIG. 26 is yet another of many embodiments of a power profile for vaporization of an oil according to the disclosure.

With continuing reference to FIGS. 1-19, and specific reference to FIGS. 20-26, one or more methods and systems for controlling a vaporizer will now be described in further detail. As discussed above, a vaporizer according to the disclosure, such as vaporizer 100 or vaporizer 200, can at least partially prevent or minimize carbonization or burning of oil, such as by at least partially preventing oil from reaching a carbonization temperature. In at least one embodiment, this can be accomplished in whole or in part by controlling at least a portion of the vaporizer, such as the heating element or heating system (e.g., heater 106, 206), so that oil reaches a vaporization temperature but does not reach a carbonization temperature. FIGS. 20-26 are described in conjunction with one another.

In at least one embodiment, a method of controlling a vaporizer can include controlling one or more components, such as heater 106, 206 or another heating system, via Pulse Width Modulation (PWM), which can include PWM driving of one or more coils 226. In such an embodiment, a method can include at least partially preventing coil 226 (or another heat source, such as laser 140) from exceeding a temperature that can cause burning of oil and/or breakdown of one or more materials, which can be a source for bad tastes or smoke during use of a vaporizer. In at least one embodiment, a PWM system 400 can control the power sent to one or more coils 226 accurately and can be controlled by one or more controllers 402, such as a microprocessor or other processor, for example. In at least one embodiment, a method can include bringing one or more coils 226 up to a vaporizing temperature and decreasing the power for maintaining such a temperature without letting the coil get hot enough to damage or burn the oil. For instance, in at least one embodiment, power to a coil can start out with a 95% signal and then drop to a 50% signal to hold a temperature over time (see FIG. 21). As another example, a method can include starting out with an 80% signal or a 100% and dropping to a 30% or other signal after a period of elapsed time to hold a vaporization temperature over time (see, e.g., FIG. 23). As a further example, PWM system 400 (if present) can be configured for modulating a power profile or power delivery by way of one or more pulse width changes over time. For instance, in at least one embodiment, PWM system 400 can be configured to implement a 95% pulse width for a first period of time (e.g., 0.1 second or about 0.1 second), such as upon activation of a vaporizer, for relatively quickly bringing oil to a vaporization temperature, and to implement a smaller pulse width (e.g., 30%) for a second period of time for maintaining a vaporization temperature during use or a period of use of the vaporizer by a user (see, e.g., FIG. 22). However, these are just examples and, as will be understood by a person of ordinary skill in the art having the benefits of the present disclosure, the starting signal and maintenance signals can be any signals required or desired for a physical embodiment of the disclosure, and can be determined based on consideration of applicable variables for an embodiment of a vaporizer according to the disclosure, such as, but not limited to, oil or material type, feeder type, heater type, volume, target temperatures, or any of the other variables described herein, separately or in combination, in whole or in part. In at least one embodiment, controller 402 can be configured to determine or control the slope of a maintenance phase of temperature control as a function of a temperature of one or more components of a vaporizer over time, such as, for example, a temperature of one or more feeders 110, 210, filters 113, 213 or, as another example, one or more tabs 350 (see, e.g., FIG. 24).

Further examples of power profiles for controlling vaporizers according to the disclosure are shown in FIGS. 25 and 26 for illustrative purposes. In at least one embodiment, controller 402 can be configured for varying voltage delivered to a heater, such as coil 226 or another heat source, over time to control the heating of oil during use of a vaporizer. For example, a first voltage, which can be a full voltage (such as 3.7 volts or another voltage), can be applied for a first time period (e.g., 0.1 second to 0.45 second or another time period) for heating oil to a target temperature, such as a vaporization temperature, relatively quickly. One or more other voltages, such as a reduced second voltage (e.g., 1.2 to 3 volts for a coil resistance range of 2.0 Ohms to 2.4 Ohms), can be delivered for a second time period for maintaining a temperature, such as a target temperature, of the oil during use of the vaporizer while at least partially reducing the likelihood of overheating or burning of the oil. The voltages and time periods can depend on the type of oil used in the vaporizer. Once again, the above mentioned time periods and voltages are described herein for illustrative purposes, and such variables can, and likely will, vary from one physical embodiment of a vaporizer 100, 200 to another, depending, for example, on the size, purpose, materials, power source, and oil type of the device. FIG. 26 illustrates the principles and methods described above in more general terms.

One or more of the oils used with the systems and methods disclosed herein can be sticky, can range in viscosity, and/or can change viscosity upon or with exposure to air, temperature changes, or other outside influences. In at least one embodiment, a vaporizer according to the disclosure can exhibit improved functionality over conventional devices in light of the foregoing oil characteristics. In at least one embodiment, a vaporizer can include a feed mechanism comprising an oil storage, such as an oil reservoir, an oil loading or feeding device, and a cap. In at least one embodiment, a vaporizer can include a wicking device, which can include one or more paths for moving oil, such as to a location for vaporization, or one or more materials for conducting oil, separately or in combination, in whole or in part. In at least one embodiment, a vaporizer can include a supply or feeder, such as a capillary supply, which can be exposed to a heat supply or heat source for vaporizing oil. In at least one embodiment, a vaporizer can include one or more of a filling device, such as a fluid inlet, a mouth piece, and an air channel or air flow path. In at least one embodiment, a vaporizer can include a heater, which can be part of a heat device or mechanism, and which can include one or more of an electrically heated wire or coil, a laser, a sonar device, or a sonic vibration device. In at least one embodiment, a vaporizer can include one or more chambers, which can include a vapor or vaporization chamber, such as chamber wherein oil can be vaporized, which can include oil being changed from a liquid to a suspension of droplets, such as droplets suspended or otherwise disposed in air within or flowing through at least a portion of a vaporizer. In at least one embodiment, a vaporizer can include one or more power supplies, which can include one or more batteries and, for example, electronics adapted for controlling one or more aspects of vaporizer operation, including, but not limited to, electronics for controlling temperature, which can include via feed-back sensors, microprocessors for control timing and displays, recharging circuitry and controls, and any other function or operation of one or more of the vaporizers, systems or methods disclosed herein, separately or in combination, in whole or in part.

In at least one embodiment, a vaporizer can include one or more reservoirs for holding oil, one or more chambers for holding vapor, one or more feeders for feeding oil from a reservoir to a chamber, and one or more heaters for heating oil. A heater can include at least one of a laser, a resistance heater, a wire, a coil, a wire at least partially disposed in a housing, and a combination thereof. A feeder can include one or more capillaries or other structures for moving fluid by capillary action. A vaporizer can be adapted to heat oil with at least one of a tube furnace, a laser furnace, a wire, a coil, and a combination thereof. A vaporizer can include any one or more of the components or portions as shown or described herein, including by way of the figures. In at least one embodiment, a method of vaporizing oil can include feeding oil from a reservoir to a chamber, and heating at least a portion of an amount of oil to a vaporization temperature. A method can include moving oil by capillary action. A method can include heating oil with at least one of a laser, a resistance heater, a wire, a coil, a wire at least partially disposed in a housing, and a combination thereof. A method can include heating oil with at least one of a tube furnace, a laser furnace, a wire, a coil, and a combination thereof. A method of vaporizing oil can include using a vaporizer as shown or described herein. A method can include using any of the one or more vaporizer components or portions shown or described herein. A method can include making, forming, manufacturing, or producing a vaporizer as shown or described herein or any of the one or more vaporizer components or portions shown or described herein. A method of storing oil can include storing oil in a device or structure as shown or described herein. In at least one embodiment, a furnace for a vaporizer can include one or more lasers, one or more lenses, one or more vapor chambers, and one or more feeds. A furnace for a vaporizer can include one or more bases, one or more tops, one or more wires, and one or more conductors. An oil storage device can include a tab adapted to couple with oil. An oil storage device can include a porous tab adapted to store oil in one or more pores thereof. A vaporizer can be adapted to couple with a tab having oil disposed at least partially therein. A vaporizer can be adapted to heat at least a portion of one or more tabs or other oil storage devices disposed at least partially therein or otherwise coupled thereto.

A vaporizer can include a reservoir for holding oil, a chamber for holding vapor, a feeder for feeding oil from the reservoir to the chamber, and a heater for heating oil. A feeder can be configured to feed oil from the reservoir to the chamber by capillary action. A feeder can include a wick that can be at least one of ceramic, sintered metal, aluminum oxide, which can include aluminum oxide held together with quartz glass or another bonding material or agent, and a combination thereof. A vaporizer can include a plug sealingly coupled to the reservoir and configured to slide relative to at least a portion of the reservoir. A plug can be configured to move from a first end of the reservoir toward the feeder as a volume of oil within the reservoir decreases. A plug can be configured to at least partially resist sinking into a volume of oil within the reservoir, such as by at least partially floating or by way of being mechanically or otherwise constrained. A vaporizer can include a feed control mount coupled to the reservoir and the chamber and configured to hold the feeder in fluid communication with the reservoir and the chamber. A heater can include at least one of a laser, a resistance heater, a wire, a coil, a wire at least partially disposed in a housing, and a combination thereof.

A vaporizer can include a controller coupled to the heater and can be configured to heat the heater to a first temperature for a first time period, reduce the temperature of the heater, and maintain the heater at a second temperature for a second time period. A first time period can be shorter or longer than a second time period. A controller can be configured to control one or more heaters by at least one of controlling voltage supplied to the heater, controlling current supplied to the heater, and a combination thereof. A controller can be configured to control one or more heaters by pulse width modulation of power supplied to the heater(s).

A reservoir can be disposed in a reservoir housing, and a reservoir housing can include a first flow passage or other passages in fluid communication with a chamber or other portion of a vaporizer. A vaporizer can include a mouthpiece coupled to the reservoir housing, and a mouthpiece can include a second flow passage or other passages in fluid communication with a first flow passage. A heater can be configured to heat at least a portion of the feeder. A vaporizer or portion thereof, such as a feeder, can be, include, or be configured to couple with a porous tab adapted to store oil in one or more pores thereof. A tab can be at least one of ceramic, sintered metal, aluminum oxide and a combination thereof. A vaporizer can include a filter coupled to the feeder or another component, such as a feed control mount, and a heater can be configured to heat at least a portion of the filter.

A vaporizer can include a reservoir housing comprising a reservoir configured to hold oil and a first flow passage fluidically separate from the reservoir, a feed control mount coupled to the reservoir housing, a chamber coupled to the feed control mount and configured to hold vapor, an air inlet disposed in the chamber, a feeder coupled to the feed control mount and disposed in fluid communication with both the reservoir and the chamber, a heater configured to heat oil disposed within the chamber, and a plug slideably and sealingly coupled to the reservoir.

A feeder can be configured to feed oil from the reservoir to the chamber, which can include by capillary action. A plug can be configured to move from a first end of the reservoir toward the feeder as a volume of oil within the reservoir decreases, such as during use of the vaporizer. A vaporizer can include a controller coupled to the heater and can be configured to heat the heater to a first temperature for a first time period, reduce the temperature of the heater, and maintain the heater at a second temperature for a second time period. A second time period can be shorter than, longer than, or equal to a first time period.

Other and further embodiments utilizing one or more aspects of the systems and methods described herein can be devised without departing from the spirit of Applicants' disclosure. For example, the systems and methods disclosed herein can be used alone or to form one or more parts of other vaporizers or vaporizing systems. Further, the various methods and embodiments of the vaporizers can be included in combination with each other to produce variations of the disclosed methods and embodiments. Discussion of singular elements can include plural elements and vice-versa. References to at least one item followed by a reference to the item can include one or more items. Also, various aspects of the embodiments can be used in conjunction with each other to accomplish the goals of the disclosure.

Unless the context requires otherwise, the words "comprise," "include," and "has" (including variations and conjugations thereof, such as "comprises," "including," "have" and so forth) should be understood to imply the inclusion of at least the stated element or step or group of elements or steps or equivalents thereof, and not the exclusion of a greater numerical quantity or any other element or step or group of elements or steps or equivalents thereof. The devices, apparatuses and systems can be used in a number of directions and orientations. The order of steps can occur in a variety of sequences unless otherwise specifically limited. The various steps described herein can be combined with other steps, interlineated with the stated steps, and/or split into multiple steps. Similarly, elements have been described functionally and can be embodied as separate components and/or can be combined into components having multiple functions.

The embodiments have been described in the context of preferred and other embodiments and not every embodiment of Applicants' disclosure has been described. Obvious modifications and alterations to the described embodiments are available to those of ordinary skill in the art having the benefits of the present disclosure. The disclosed and undisclosed embodiments are not intended to limit or restrict the scope or applicability of Applicants' disclosures, but rather, in conformity with the patent laws, Applicants intend to fully protect all such modifications and improvements that come within the scope or range of equivalents of the following claims.

What is claimed is:

1. A vaporizer, comprising:
   a first end comprising a mouthpiece or configured to be coupled to a mouthpiece;
   a second end longitudinally opposite the first end;
   a reservoir housing comprising a reservoir for holding oil;
   a plug sealingly coupled to an internal surface of the reservoir housing and configured to slide relative to at least a portion of the reservoir housing;
   a chamber for holding vapor;
   a feeder for feeding oil from the reservoir toward the chamber; and
   a feed control mount disposed at least partially between the reservoir and the chamber and configured to hold the feeder in fluid communication with the reservoir and the chamber;
   wherein the feeder is coupled to the feed control mount;
   wherein the feeder is at least partially porous and is configured to feed oil from the reservoir toward the chamber by capillary action; and
   wherein the plug is configured to slide in a first direction away from the first end of the vaporizer and toward the second end of the vaporizer as a volume of oil within the reservoir decreases.

2. The vaporizer of claim 1, wherein the feeder is a porous body having a top surface in fluid communication with the reservoir, a bottom surface in fluid communication with the chamber and at least one radially exterior surface, and wherein the feeder is configured to feed oil in the first direction.

3. The vaporizer of claim 2, further comprising a laser heater coupled to the second end and having a laser configured to direct a beam onto the porous body.

4. The vaporizer of claim 3, wherein the reservoir is configured to hold oil having a vaporization temperature, and wherein the laser is configured to heat at least a portion of the porous body to a temperature that is greater than or equal to the vaporization temperature.

5. The vaporizer of claim 3, further comprising a lens configured to concentrate laser light onto the porous body.

6. The vaporizer of claim 2, wherein the porous body is disposed outside of the reservoir and within the feed control mount.

7. The vaporizer of claim 1, further comprising a volume of oil disposed within the reservoir, and wherein the plug is configured to move toward the feeder as the volume of oil within the reservoir decreases.

8. The vaporizer of claim 7, wherein the plug is configured to at least partially float in the volume of oil within the reservoir.

9. The vaporizer of claim 1, wherein the second end is configured to couple to a heater that comprises at least one of a laser, a resistance heater, a wire, a coil, a wire at least partially disposed in a housing, and a combination thereof.

10. The vaporizer of claim 1, further comprising a controller coupled to the heater, and wherein the vaporizer is configured to
heat the feeder to a first temperature for a first time period;
reduce an amount of heat applied to the feeder; and
maintain the feeder at a second temperature for a second time period;
wherein the first time period and the second time period differ.

11. The vaporizer of claim 10, wherein the controller is configured to control the heater by at least one of controlling voltage supplied to the heater, controlling current supplied to the heater, pulse width modulation of power supplied to the heater, and a combination thereof.

12. The vaporizer of claim 1, wherein the feed control mount has a first side coupled to the reservoir housing and wherein the reservoir is disposed longitudinally between the first end of the vaporizer and at least a portion of the feed control mount.

13. The vaporizer of claim 1, wherein the feeder comprises a porous body configured to store oil in one or more pores thereof, wherein the porous body has a top surface, a bottom surface and at least one radially exterior surface, and wherein each of the top surface, the bottom surface and the at least one radially exterior surface comprises a plurality of pores.

14. The vaporizer of claim 13, wherein the plurality of pores of the at least one radially exterior surface comprises a plurality of pores in contact with an interior surface of the feed control mount.

15. The vaporizer of claim 1, further comprising a filter coupled to the feeder and configured to filter oil exiting the feeder.

16. The vaporizer of claim 1, further comprising a heater coupled to the second end of the vaporizer, wherein the heater is configured to heat at least a portion of the feeder.

17. The vaporizer of claim 1, wherein the feeder is disposed entirely within the feed control mount.

18. A vaporizer, comprising:
a first end comprising a mouthpiece or configured to be coupled to a mouthpiece;
a second end longitudinally opposite the first end and configured to couple with a heater;
a reservoir housing comprising a reservoir configured to hold oil;
a feed control mount coupled to the reservoir housing;
a chamber fluidically coupled to the feed control mount and configured to hold vapor;
an air inlet in fluid communication with the chamber;
a porous body coupled to the feed control mount and disposed in fluid communication with both the reservoir and the chamber; and
a plug slideably and sealingly coupled to an interior surface of the reservoir;
wherein the porous body is configured to feed oil from the reservoir toward the chamber by capillary action; and
wherein the plug is configured to move in a first direction away from the first end of the vaporizer and toward the feed control mount as a volume of oil within the reservoir decreases.

19. The vaporizer of claim 18, further comprising a heater coupled to the second end, wherein the heater comprises a controller coupled to a laser, and wherein the vaporizer is configured to
heat the porous body to a first temperature for a first time period;
reduce an amount of heat applied to the porous body; and
maintain the porous body at a second temperature for a second time period.

20. A vaporizer, comprising:
a first end configured to couple with a mouthpiece;
a second end longitudinally opposite the first end and configured to be coupled with a heater and a power source;
a reservoir housing comprising a reservoir configured to hold oil, wherein the reservoir is disposed longitudinally between the first and second ends of the vaporizer;
a feed control mount coupled to the reservoir housing;
a chamber fluidically coupled to the feed control mount and configured to hold vapor, wherein the chamber is disposed longitudinally between at least a portion of the feed control mount and the second end of the vaporizer;
an air inlet through a wall of the chamber;
a porous feeder disposed at least partially within the feed control mount in fluid communication with both the reservoir and the chamber; and
a plug slideably and sealingly coupled to an interior surface of the reservoir housing; wherein the feeder is disposed longitudinally between the reservoir and the chamber; wherein at least a portion of the feed control mount is disposed longitudinally between the reservoir and the chamber;
wherein the feeder is configured to feed oil by capillary action from the reservoir to an exterior surface of the feeder in fluid communication with the chamber;
and wherein the plug is configured to slide in a first direction away from the first end of the vaporizer and toward the feeder as a volume of oil within the reservoir decreases.

* * * * *